(12) United States Patent
Pedrussio et al.

(10) Patent No.: US 12,144,861 B2
(45) Date of Patent: Nov. 19, 2024

(54) PHARMACEUTICAL PRODUCT WITH INCREASED STABILITY COMPRISING IMMUNOGLOBULINS

(71) Applicant: CSL BEHRING AG, Bern (CH)

(72) Inventors: Renzo Pedrussio, Koeniz (CH); Regula Styger, Bern (CH)

(73) Assignee: CSL Behring AG, Bern (CH)

( * ) Notice: Subject to any disclaimer, the term of this patent is extended or adjusted under 35 U.S.C. 154(b) by 0 days.

(21) Appl. No.: 15/532,378

(22) PCT Filed: Dec. 3, 2015

(86) PCT No.: PCT/EP2015/078482
§ 371 (c)(1),
(2) Date: Jun. 1, 2017

(87) PCT Pub. No.: WO2016/087569
PCT Pub. Date: Jun. 9, 2016

(65) Prior Publication Data
US 2018/0264111 A1  Sep. 20, 2018

(30) Foreign Application Priority Data
Dec. 3, 2014  (EP) .................... 14196069

(51) Int. Cl.
| A61K 39/395 | (2006.01) |
| A61M 5/00 | (2006.01) |
| B65D 25/14 | (2006.01) |
| B65D 75/36 | (2006.01) |
| B65D 81/26 | (2006.01) |
| B65D 81/30 | (2006.01) |
| C07K 16/00 | (2006.01) |

(52) U.S. Cl.
CPC ....... *A61K 39/39591* (2013.01); *A61M 5/002* (2013.01); *B65D 25/14* (2013.01); *B65D 75/36* (2013.01); *B65D 81/268* (2013.01); *B65D 81/30* (2013.01); *C07K 16/00* (2013.01); *C07K 2317/10* (2013.01); *C07K 2317/21* (2013.01); *C07K 2317/94* (2013.01)

(58) Field of Classification Search
None
See application file for complete search history.

(56) References Cited

U.S. PATENT DOCUMENTS

| 4,186,192 A | 1/1980 | Lundblad et al. |
| 4,360,451 A | 11/1982 | Schmolka |
| 4,362,661 A | 12/1982 | Ono et al. |
| 4,396,608 A | 8/1983 | Tenold |
| 4,439,421 A | 3/1984 | Hooper et al. |
| 4,499,073 A | 2/1985 | Tenold |
| 4,849,508 A | 7/1989 | Magnin et al. |
| 4,880,913 A | 11/1989 | Doleschel et al. |
| 5,164,487 A | 11/1992 | Kothe et al. |
| 5,177,194 A | 1/1993 | Sarno et al. |
| 5,503,827 A | 4/1996 | Woog et al. |
| 5,593,675 A | 1/1997 | Hodler et al. |
| 5,871,736 A | 2/1999 | Bruegger et al. |
| 5,945,098 A | 8/1999 | Sarno et al. |
| 6,069,236 A | 5/2000 | Burnouf-Radosevich et al. |
| 6,093,324 A | 7/2000 | Bertolini et al. |
| 6,162,904 A | 12/2000 | Mamidi et al. |
| 6,171,586 B1 | 1/2001 | Lam et al. |
| 6,252,055 B1 | 6/2001 | Relton |
| 6,303,113 B1 | 10/2001 | Woog et al. |
| 8,715,652 B2 * | 5/2014 | Bolli .................... A61K 9/0019 424/130.1 |
| 8,906,368 B2 | 12/2014 | Bolli et al. |
| 9,241,897 B2 | 1/2016 | Bolli et al. |
| 9,422,364 B2 | 8/2016 | Maeder et al. |
| 10,434,176 B2 | 10/2019 | Maeder et al. |
| 2005/0075611 A1 * | 4/2005 | Hetzler ................. A61L 2/0011 604/192 |
| 2005/0142139 A1 | 6/2005 | Schulke et al. |
| 2005/0276823 A1 * | 12/2005 | Cini ...................... A61K 47/18 424/400 |
| 2006/0051347 A1 | 3/2006 | Winter |
| 2006/0076536 A1 * | 4/2006 | Barshied ............. C01B 13/0233 252/188.28 |
| 2007/0122402 A1 * | 5/2007 | Bolli .................... A61K 9/0019 424/133.1 |
| 2008/0072992 A1 | 3/2008 | Baleriaux et al. |
| 2011/0060290 A1 * | 3/2011 | Bonk ................... A61K 9/0019 604/181 |
| 2013/0017191 A1 | 1/2013 | Maeder et al. |
| 2013/0102760 A1 | 4/2013 | Bolli et al. |

(Continued)

FOREIGN PATENT DOCUMENTS

| AU | 2004290899 B2 | 3/2010 |
| CA | 2272245 A1 | 5/1998 |
| DE | 2364792 | 7/1974 |

(Continued)

OTHER PUBLICATIONS

Hlzentra product insert, CSL Bering, p. 1-49 (Year: 2011).*
FDA approves Hlzentra, Drugs.com/newdrugs/csl-behring-receives-fda-approval-hizentra-first-20-percent-subcutaneous-immunoglobulin-therapy-2037.html, p. 1-4, 2010.*
Jolles et al. Adv Ther 2011, vol. 28(7), pp. 521-533, (Year: 2011).*
PharmaEd's 7th Annual Pre-Filled Syringes Forum, Strategic Development, Safety & Regulatory Compliance, and Commercialization of Pre-Filled Syringes, May 19-20, 2014, Philadelphia, PA, 8 pages.

(Continued)

*Primary Examiner* — Yunsoo Kim
(74) *Attorney, Agent, or Firm* — McNeill PLLC

(57) ABSTRACT

The present invention pertains to a pharmaceutical product comprising a polyclonal immunoglobulin solution in a prefilled polymer syringe in secondary packaging comprising an oxygen scavenger.

31 Claims, 4 Drawing Sheets

(56) References Cited

U.S. PATENT DOCUMENTS

2015/0224264 A1     8/2015     Arvis

FOREIGN PATENT DOCUMENTS

| | | |
|---|---|---|
| DE | 3430320 A1 | 3/1985 |
| DE | 4118912 C1 | 7/1992 |
| EP | 0025275 A2 | 3/1981 |
| EP | 0037078 A2 | 10/1981 |
| EP | 0187712 | 7/1986 |
| EP | 0196761 | 10/1986 |
| EP | 0392717 | 10/1990 |
| EP | 0437622 | 7/1991 |
| EP | 0528313 | 2/1993 |
| EP | 0447585 | 5/1995 |
| EP | 0702960 | 3/1996 |
| EP | 0852951 | 7/1998 |
| EP | 0893450 | 1/1999 |
| EP | 0911037 | 4/1999 |
| EP | 1268551 | 2/2004 |
| EP | 1084147 | 9/2004 |
| EP | 1532983 | 5/2005 |
| EP | 2 361 636 A1 | 8/2011 |
| EP | 3 202 389 A1 | 9/2017 |
| FR | 2 995 213 A1 | 3/2014 |
| GB | 2 471 726 A | 1/2011 |
| JP | S5420124 | 2/1979 |
| JP | S56127321 | 10/1981 |
| JP | S5731623 | 2/1982 |
| JP | S57128635 | 8/1982 |
| JP | 60120823 | 6/1985 |
| JP | 61194035 | 8/1986 |
| JP | H04346934 | 12/1992 |
| JP | 05178719 | 7/1993 |
| JP | H06510031 | 11/1994 |
| JP | H0899899 | 4/1996 |
| JP | H10502938 | 3/1998 |
| JP | 2001503781 | 3/2001 |
| JP | 2001519770 | 10/2001 |
| WO | 199429334 | 12/1994 |
| WO | 199607429 | 3/1996 |
| WO | 199615153 | 5/1996 |
| WO | 199805686 | 2/1998 |
| WO | 199828007 | 7/1998 |
| WO | 199964462 | 12/1999 |
| WO | 2002080976 | 10/2002 |
| WO | 2002096457 A2 | 12/2002 |
| WO | WO 2003/039632 A2 | 5/2003 |
| WO | 2004084816 | 10/2004 |
| WO | 2005049078 | 6/2005 |
| WO | 2007100396 A2 | 9/2007 |
| WO | 2008039761 | 4/2008 |
| WO | 2011034604 A2 | 3/2011 |
| WO | 2011088120 A1 | 7/2011 |
| WO | 2011104315 | 9/2011 |
| WO | WO 2011/104315 A2 | 9/2011 |
| WO | 2011034604 A9 | 1/2012 |
| WO | WO 2012/022734 A2 | 2/2012 |
| WO | WO 2012/151247 A2 | 11/2012 |
| WO | WO 2014-041307 A1 | 3/2014 |
| WO | WO 2014/140095 A1 | 9/2014 |
| WO | WO 2014/140097 A1 | 9/2014 |
| WO | 2016087569 A1 | 6/2016 |

OTHER PUBLICATIONS

"Relative Density," European Pharmacopoeia 5.0, Reference Index 2.2.5, pp. 27-28 (2004).
"Size-Exclusion Chromatography," European Pharmacopoeia 5.0, Reference Index 2.2.30, p. 45 (2004).
"Chromatographic Separation Techniques", European Pharmacopoeia 5.0, Reference Index 2.2.46, pp. 69-73 (2004).
"Pekallikrein Activator," European Pharmacopoeia 5.0, Reference Index 2.6.15, pp. 168-169 (2004).
"Test For Fc function of Immunoglobulin," European Pharmacopoeia 5.0, Reference Index 2.7.9, pp. 202-203 (2004).
"Human Albumin Solution," European Pharmacopoeia 5.0, pp. 1731-1732 (2004).
"Human Normal Immunoglobulin For Intravenous Administration," European Pharmacopoeia 5.0, pp. 1744-1745 (2014).
Shin, J.Y. et al., "Chemical Structure And Physical Properties of Cyclic Olefin Copolymers", International Union Of Pure And Applied Chemistry, Polymer Division, *Pure Appl. Chem.*, vol. 77. No. 5, pp. 801-814 (2005).
Shapiro, R.S., "Subcutaneous immunoglobulin therapy given by subcutaneous rapid push vs infusion pump: a retrospective analysis," *Ann Allergy Asthma Immunol*, Elsevier, pp. 1-5 (2013).
"Specific Gravity", Physical Tests, vol. 841, p. 1.
European Search Report and Annex to European Search Report, issued by the European Patent Office in Application No. 14196069.0, dated Feb. 20, 2015 (8 pages).
International Search Report issued by the European Patent Office in International Application No. PCT/EP2015/078482, mailed Feb. 22, 2016 (7 pages).
Written Opinion of the International Searching Authority, issued by the European Patent Office in International Application No. PCT/EP2015/078482, mailed Feb. 22, 2016 (6 pages).
Badkar et al., "Development of Biotechnology Products in Pre-filled Syringes: Technical Considerations and Approaches," AAPS Pharm. Sci. Tech., 2011, 12(2): 564-572.
Bee et al., "Effects of Surfaces and Leachables on the Stability of Biopharmaceuticals," Journal of Pharmaceutical Sciences, 2011, 100: 4158-4170.
Cramer et al., "Stability over 36 months of a new liquid 10% polyclonal immunoglobulin product (IgPro10, Privigen©) stabilized with L-proline," Vox Sanguinis, 2009, 1-7.
Daugherty et al., "Formulation and delivery issues for monoclonal antibody therapeutics," Advanced Drug Delivery Reviews, 2006, 58: 686-706.
Davies et al., "Photo-oxidation of proteins and its role in cataractogenesis," Journal of Photochemistry and Photobiology B: Biology, 2001, 63: 114-125.
Krayukhina et al., "Effects of Syringe Material and Silicone Oil Lubrication on the Stability of Pharmaceutical Proteins," Journal of Pharmaceutical Sciences, 2015, 104: 527-535.
FDA Guidance for Industry: Container Closure Systems for Packaging Human Drugs and Biologics, 1999, 56 pages.
International Conference on Harmonization (ICH), Topic Q6A, Specifications: Test Procedures and Acceptance Criteria for New Drug Substances and New Drug Products: Chemical Substances, 1999, 32 pages.
Jezek et al., "Biopharmaceutical formulations for pre-filled delivery devices," Expert Opinion on Drug Delivery, 2013, 10(6): 811-828.
Sacha et al., "Practical fundamentals of glass, rubber, and plastic sterile packaging systems," Pharmaceutical Development and Technology, 2010, 15(1): 6-34.
Sharma, "Immunogenicity of therapeutic proteins. Part 2: Impact of container closures," Biotechnology Advances, 2007, 25: 318-324.
Wang et al., "Antibody Structure, Instability, and Formulation," Journal of Pharmaceutical Sciences, 2007, 96: 1-26.
Reply Brief under Board Rule § 41.41 and Request for Oral Hearing, filed Feb. 21, 2012, for U.S. Appl. No. 10/579,357.
Auxiliary requests submitted in response to Notice of Opposition to European Patent 2 531 218 B1, submitted Feb. 12, 2020 (31 pages).
Reply to Office Action, filed Mar. 14, 2014, for U.S. Appl. No. 13/618,757.
Request for Continued Examination and Reply to Office Action under 37 C.F.R. § 1.114, filed Sep. 17, 2010, for U.S. Appl. No. 10/579,357.
CSL Behring press release of Feb. 24, 2011 (2 pages) (Document D18 submitted Mar. 7, 2014, with Patent Owner's Response to Notice of Opposition submitted Mar. 7, 2014, for European Patent No. 1687028 B1 (Application No. 04818790.0-1412)).
"Peptide Storage and Handling Guidelines" GenScript, The Biology CRO, (accessed from https://www.genscript.com/peptide_storage_and_handling.html on Oct. 13, 2020).
Response to Restriction Requirement, filed Jun. 12, 2008, for U.S. Appl. No. 10/579,357.

(56) References Cited

OTHER PUBLICATIONS

Restriction Requirement mailed May 12, 2008, for U.S. Appl. No. 10/579,357.
Samuel et al., "Proline Inhibits Aggregation During Protein Refolding," Protein Science, 9: 344-352 (2000).
Samuel et al., "Proline is a Protein Solubilizing Solute," Biochemistry and Molecular Biology International, 41(2): 235-242 (1997).
Scopes, "Protein Purification, Principles and Practice," 2nd Edition, pp. 42-45, in "Springer Advance Texts in Chemistry," Charles R. Cantor Ed., Springer-Verlag, N.Y. (1987).
Shiraki et al., "Biophysical Effect of Amino Acids on the Prevention of Protein Aggregation," J. Biochem., 132(4): 591-595 (2002).
Shire et al., "Challenges in the Development of High Protein Concentration Formulations", Journal of Pharmaceutical Sciences, 93(6), pp. 1390-1402 (Jun. 2004).
Smith, L.T., "Characterization of a .gamma.-Glutamyl Kinase from *Escherichia coli* That Confers Proline Overproduction and Osmotic Tolerance," Journal of Bacteriology, 164(3): 1088-1093 (1985).
Spycher et al., "Well-tolerated liquid intravenous immunoglobulin G preparations (IVIG) have a low immunoglobulin G dimer (IgG-dimer) content," J. Autoimmun. 96 (Suppl. 1): 96 (1996).
Stucki et. al., "Characterisation of a Chromatographically Produced Anti-D Immunoglobulin Product," J. Chromatograph B., 700: 241-248 (1997).
Summons to attend oral proceedings pursuant to Rule 115(1) EPC, mailed Jun. 13, 2014, for EP Patent No. 1687028 (17 pages).
Supplemental Proprietor's submission filed Apr. 17, 2014, for European Patent No. 1687028 B1 (Application No. 04818790.0-1412) (7 pages).
Taneja et al., "Increased Thermal Stability of Proteins in the Presence of Amino Acids," Biochem. J., 303: 147-153 (1994).
Tankersley et al., "Immunoglobulin G Dimer: An Idiotype-Anti-Idiotype Complex," Molecular Immunology, 25(1): 41-48 (1988).
U.S. Appl. No. 61/277,045 (priority document for WO 2011/034604 listed above).
Transmittal of Labels and Circulars Mar. 28-29, 2010 from US FDA concerning Privigen (1 page) (Document D21 submitted Mar. 7, 2014, with Patent Owner's Response to Notice of Opposition submitted Mar. 7, 2014, for European Patent No. 1687028 B1 (Application No. 04818790.0-1412).
U.S. Department of Health and Human Services, Food and Drug Administration, Center for Drug Evaluation and Research (CDER), Center for Biologics Evaluation and Research (CBER), "Guidance for Industry Q1A(R2) Stability Testing of New Drug Substances and Products, Revision 2," Nov. 2003 (25 pages).
U.S. Food and Drug Administration package insert for HIZENTRA, Immune Globulin Subcutaneous (Human), 20% Liquid, issued Feb. 2010 (26 pages).
U.S. Food and Drug Administration package insert for PRIVIGENTM, Immune Globulin Intravenous (Human), 10% Liquid, issued Jul. 2007 (20 pages).
Tankersley, "Dimer Formation in Immunoglobulin Preparations and Speculations on the Mechanism of Action of Intravenous Immune Globulin in Autoimmune Diseases," Immunological Reviews 139: 159-172 (1994).
USPTO Prosecution History of U.S. Appl. No. 13/577,220.
USPTO Prosecution History of U.S. Appl. No. 14/970,326.
Letter from EMEA concerning Hizentra (3 pages) (Document D19 submitted Mar. 7, 2014, with Patent Owner's Response to Notice of Opposition submitted Mar. 7, 2014, for European Patent No. 1687028 B1 (Application No. 04818790.0-1412)).
Letter from US FDA concerning Hizentra (2 pages) (Document D20 submitted Mar. 7, 2014, with Patent Owner's Response to Notice of Opposition submitted Mar. 7, 2014, for European Patent No. 1687028 B1 (Application No. 04818790.0-1412)).
Maeder et al., "Stability over 24 Months and Tolerability of a New 20% Proline-stabilized Polyclonal Immunoglobulin for Subcutaneous Administration (SCIG)", J Allergy Clin Immunol, AB142 Abstracts (Feb. 2010).

PCT Written Opinion mailed May 18, 2005, for International Patent Application No. PCT/EP2004/013022 (6 pages).
Extended European Search Report dated May 4, 2012, for European Patent Application No. 10177786.0 (9 pages).
Certified Priority Document EP Patent Appl. No. 03026539.1, filed Nov. 18, 2003 (27 pages).
"2.2.2. Degree of Coloration of Liquids," from European Pharmacopoeia 5.0, Supplement 5.5, pp. 24-26, Jul. 2006.
Reply to Office Action, filed Feb. 16, 2010, for U.S. Appl. No. 10/579,357.
Abbas et al., Cellular and Molecular Immunology 4.sup.th Ed. 2000, cover pages and pp. 470 and 482.
Advisory Action, mailed Aug. 7, 2009, for U.S. Appl. No. 10/579,357.
Ahrer et al., "Effects of ultra-/diafiltration conditions on present aggregates in human immunoglobulin G preparations", Journal of Membrane Science, 274, pp. 108-115 (2006).
Alberts et al., Molecular Biology of the Cell 3.sub.rd Ed. 1994, cover pages and p. G-12.
Amendment and Response under 37 C.F.R § 1.116, filed Aug. 4, 2009, for U.S. Appl. No. 10/579,357.
Andersson et al., "An Improved Chromatography Method for Production of IgG from Human Plasma," Presented at XXIII Congress of the International Society of Blood Transfusion (1994).
Andresen et al., "Product equivalence study comparing the tolerability, pharmacokinetics, and pharmachodynamics of various human immunoglobulin-G formulations," J. Clin Pharmacol, vol. 40, pp. 722-730 (2000).
Anonymous, "2.2.49 Falling ball viscometer method", European Pharmacopoeia 6.0, p. 84 (2007).
Appeal Brief under Board Rule § 41.37, filed Oct. 3, 2011, for U.S. Appl. No. 10/579,357.
Arakawa et al., "Protein-Solvent Interactions in Pharmaceutical Formulations," Pharmaceutical Research, 8(3): 285-291 (1991).
Arakawa et al., "The Stabilization of Proteins by Osmolytes," Biophys. J., 47: 411-414, (1985).
Australian Patent Examination Report No. 2; Application No. 2011219828 dated Sep. 3, 2014.
Request for Continued Examination, filed Sep. 3, 2009, for U.S. Appl. No. 10/579,357.
Azulay et al., "Intravenous Immunoglobulin Treatment in Patients With Motor Neuron Syndromes Associated With Anti-GM.sub. 1 Antibodies, A Double-Blind, Placebo-Controlled Study," Neurology, 44: 429-432 (1994).
Basta et al., "High-Dose Intravenous Immunoglobulin Exerts its Beneficial Effect in Patients with Dermatomyositis by Blocking Endomysial Deposition of Activated Complement Fragments," J. Clin. Invest., 94: 1729-1735 (1994).
Berkman et al., "Clinical Uses of Intravenous Immunoglobulins," Annals Internal Medicine, 112: 278-292 (1990).
Biesert, "Virus Validation Studies of Immunoglobulin Preparations," Clin. Exp. Rheumatol., 14(Suppl. 15): S47-S52 (1996).
Bjorkander et al., "1040 Prophylactic Infusions with an Unmodified Intravenous Immunoglobulin Product Causing Few Side-Effects in Patients with Antibody Deficiency Syndromes," Infection, 13(3): 102-110 (1985).
Bleeker et al., "An Animal Model for the Detection of Hypotensive Side Effects of Immunoglobulin Preparations," Vox Sang., 52: 281-290 (1987).
Bolli et al. "IgG-dimer formation in liquid immunoglobulin preparations is inhibited by nicotinamide and other amphiphilic compounds," J. Autoimmun. 96 (Suppl. 1): 96 (1996).
Bolli et al., "L-Proline reduces IgG dimer content and enhances the stability of intravenous immunoglobulin (IVIG) solutions," Biologicals, 38: 150-157 (2010).
Braun, J., "The Second Century of the Antibody—Molecular Perspectives in Regulation, Pathophysiology, and Therapeutic Applications", The Western Journal of Medicine, 157(2), pp. 158-168 (Aug. 1992).
Brenner, "Clinical Experience With Octagam, a Solvent Detergent (SD) Virus Inactivated Intravenous Gammaglobulin," Clin. Exp. Rheumatol., 14(Suppl. 15): S115-S119 (1996).

(56) References Cited

OTHER PUBLICATIONS

Buckley et al., "The Use of Intravenous Immune Globulin in Immunodeficiency Diseases," New Eng. J. Med., 325(2): 110-117 (1991).

Burckbuchler et al., Rheological and syringeability properties of highly concentrated human polyclonal Immunoglobulin solutions, Eur. J. Pharm. Biopharm., 76: 351-356 (2010).

Carpenter et al., "Cryoprotection of Phosphofructokinase with Organic Solutes: Characterization of Enhanced Protection in the Presence of Divalent Cations," Archives of Biochemistry and Biophysics, 250(2): 505-512 (1986).

Cassulis et al., "Ligand Affinity Chromatographic Separation of Serum IgG on Recombinant Protein G-Silica," Clin. Chem., 37(6): 882-886 (1991).

Cleland et al., "The Development of Stable Protein Formulations: A Close Look at Protein Aggregation, Deamidation, and Oxidation," Crit. Rev. Therap. Drug Carrier Systems, 10(4): 307-377 (1993).

Clerc et al., "Labelling of Colloidal Gold with IgE," Histochemistry, 89: 343-349 (1988).

Communication pursuant to Article 94(3) EPC for EP Patent App. No. 10177786.0 (3 pages).

Cooperative Group for the Study of Immunoglobulin in Chronic Lymphocytic Leukemia, "Intravenous Immunoglobulin for the Prevention of Infection in Chronic Lymphocytic Leukemia, A Randomized, Controlled Clinical Trial," New Eng. J. Med., 319: 902-907 (1998).

Response to Office Action, filed Feb. 9, 2009, for U.S. Appl. No. 10/579,357.

CSL Behring press release, "CSL Behring Receives FDA Approval to Extend Shelf Life of HizentraTM from 18 months to 24 months," Aug. 18, 2010 (2 pages).

Dalakas, "Intravenous Immune Globulin Therapy for Neurologic Diseases," Ann. Int. Med., 126(9): 721-730 (1997).

Decision on Appeal, mailed Dec. 9, 2013 for U.S. Appl. No. 10/579,357.

Declaration of Annette Gaida (7 pages) (Document D22 submitted with Patent Owner's Response to Notice of Opposition submitted Mar. 7, 2014, for European Patent No. 1687028 B1 (Application No. 04818790.0-1412).

Dwyer, "Manipulating the Immune System with Immune Globulin," New Eng. J. Med., 326(2): 107-116 (1992).

El Alaoui et al., "Development of an Immunocapture Method for Measuring IgA Antibodies to Tissue Transglutaminase in the Sera of Patients with Coeliac Disease," Clin. Exp. Immunol., 144: 101-109 (2006).

European Search Report dated Apr. 28, 2004, for European Patent Application No. 03026539.1 (10 pages).

Examiner's Answer, mailed Dec. 21, 2011, for U.S. Appl. No. 10/579,357.

Extended European Search Report and European Search Opinion for European Patent App. No. 10 001 164.2, mailed Jul. 19, 2010 (10 pages).

Extended European Search Report and European Search Opinion for European Patent App. No. 10 001 996.7, mailed Aug. 6, 2010 (5 pages).

Notice of Opposition dated Jun. 28, 2013, for European Patent No. 1687028 (21 pages).

Final Office Action, mailed May 19, 2010, for U.S. Appl. No. 10/579,357.

Final Office Action, mailed May 23, 2014, for U.S. Appl. No. 13/618,757.

Final Office Action, mailed May 5, 2009, for U.S. Appl. No. 10/579,357.

Gammagard S/D, "Humanes Immunoglobulin Zur Intravenosen Anwendung Solvent/Detergent Behandelt," Product Information, Baxter Deutschland GmbH, Edisonstr. 3-4, D-85716 Unterschleibheim, Germany (1994).

GE Healthcare, "Scale-up of a downstream monoclonal antibody purification process using HiScreenTM and AxiChromTM columns", Application Note 28-9403-49 AA (2009).

Gombotz et al., "The Stabilization of a Human IgM Monoclonal Antibody with Poly(vinylpyrrolidone)," Pharm. Res., 11(5): 624-632 (1994); Document D25 submitted Jun. 10, 2014, with Opponent's Response to Proprietor's Letter, for European Patent No. 1687028 B1 (Application No. 04818790.0-1412).

Habeeb et al., "Preparation of Human Immunoglobulin by Caprylic Acid Precipitation," Preparative Biochem., 4(1): 1-17 (1984).

Hansen et al., "Isolation and Purification of Immunoglobulins from Chicken Eggs Using Thiophilic Interaction Chromatography," J. Immunol. Meth., 215: 1-7 (1998).

Harris, Ed., "Blood Separation and Plasma Fractionation," pp. 332-333, Wiley-Liss, New York (1991).

Hazen et al., "Cryoprotection of Antibody by Organic Solutes and Organic Solute/Divalent Cation Mixtures," Archives of Biochemistry and Biophysics, 267(1): 363-371 (1988).

Hocini et al., "An ELISA Method to Measure Total and Specific Human Secretory IgA Subclasses Based on Selective Degradation by IgA1-Protease," J. Immunol. Meth., 235(1-2): 53-60 (2000) (Abstract).

Inoue et al., "Specific Decrease in Solution Viscosity of Antibodies by Arginine for Therapeutic Formulation", Mol. Pharmaceutics, 11, pp. 1889-1896 (2014).

Rejection Decision, mailed May 8, 2014, for Chinese Patent App. No. 201180010874.X (4 pages), with translation (4 pages).

International Blood/Plasma News, "CSL BEHRING announced that the U.S. FDA has approved a supplemental Biologics License Application (sBLA) that extends the shelf life of its Privigen 10% liquid intravenous immunoglobulin product from 24 months to 36 months," p. 12, Apr. 2010.

Interview Summary, mailed Aug. 19, 2010, for U.S. Appl. No. 10/579,357.

Jezek et al., "Viscosity of concentrated therapeutic protein compositions", Advanced Drug Delivery Reviews 63, pp. 1107-1117 (2011).

Kaveri et al., "Intravenous Immunoglobulins (IVIg) in the Treatment of Autoimmune Diseases," Clin. Exp. Immunol., vol. 86, pp. 192-198 (1991).

Koopman et al., "A Sensitive Radioimmunoassay for Quantitation of IgM Rheumatoid Factor," Arth. Rheum., 23(3): 302-308 (1980).

Kumar et al., "The Role of Proline in the Prevention of Aggregation During Protein Folding In Vitro," Biochem. Mol. Biol. Int., 46(3): 509-517 (1998).

Leaflet—"Falling Ball Viscosimeter", Brookfield, Viscometers/Rheometers, undated, cited in Notice of pppposition to European Patent 2 531 218 B1 filed Sep. 11, 2019.

Lemm, G., "Composition and properties of IVIg preparations that affect tolerability and therapeutic efficacy," Neurology 69(Suppl. 6): S28-S32 (2002).

Van Reis et al., "Linear Scale Ultrafiltration", Biotechnology & Bioengineering, 55, pp. 737-746 (1997).

Vermeer et al., "The Thermal Stability of Immunoglobulin: Unfolding and Aggregation of a Multi-Domain Protein," Biophys. J., 78: 394-404 (2000); Document D24 submitted Jun. 10, 2014, with Opponent's Response to Proprietor's Letter, for European Patent No. 1687028 B1 (Application No. 04818790.0-1412).

Lilie, H., "Folding of the Fab fragment within the intact antibody," FEBS Lett. 417: 239-242 (1997).

Liu et aL, "Reversible Self-Association Increases the Viscosity of a Concentrated Monoclonal Antibody in Aqueous Solution", Journal of Pharmaceutical Sciences, 94(9), pp. 1928 (2005).

Lundblad et al., "Comparative Studies of Impurities in Intravenous Immunoglobulin Preparations," The University of Chicago, Rev. Infectious Diseases, 8(Supp. 4): S382-S390 (1986).

Maeder el aL, "Stability over 24 Months and Tolerability of a New 20% Praline-stabilized Polyclonal Immunoglobulin or Subcutaneous Administration (SCIG)", J Allergy Clin Immunol, AB 142 Abstracts, Abstract No. 558 (Feb. 2010).

Waldo et al., "Mixed IgA-IgG Aggregates as a Model of Immune Complexes in IgA Nephropathy," J. Immunol., 142(11): 3841-3846 (1989).

McCue, "Changes in Therapeutic Proteins Caused by Preparation Techniques," Ann. Internal Medicine, 111(4): 271-272 (1989).

(56) References Cited

OTHER PUBLICATIONS

Misbah et al., "Subcutaneous immunoglobulin: opportunities and outlook," Clinical and Experimental Immunology, 158 (Suppl. 1): 51-59 (2009).
Mollnes et al., "Effect of Whole and Fractionated Intravenous Immunoglobulin on Complement In Vitro," Mol. Immunol., 34(10): 719-729 (1997).
Non-final Office Action, mailed Dec. 26, 2013, for U.S. Appl. No. 13/618,757.
Notice of Allowance and Fee(s) Due, mailed Aug. 5, 2014, for U.S. Appl. No. 13/618,757 (7 pages).
Notice of Allowance and Fee(s) Due, mailed Dec. 19, 2013, for U.S. Appl. No. 10/579,357.
Notice of Appeal under 37 C.F.R. § 41.31, filed Sep. 7, 2011, for U.S. Appl. No. 10/579,357.
Notice of Opposition to European Patent 2 531 218 B1, submitted Sep. 11, 2019 (27 pages).
Notice of the Reason of Rejection dispatched Jul. 13, 2010, for Japanese Patent Application No. 2006-540301 (3 pages) with translation (4 pages).
International Search Report and the Written Opinion of the International Searching Authority for International Patent App. No. PCT/EP2011/052770, mailed Jun. 9, 2011 (8 pages).
International Search Report and the Written Opinion of the International Searching Authority for International Patent App. No. PCT/EP2011/051556, mailed Feb. 28, 2011 (12 pages).
Nourichafi et al., "Comparison of various chromatographic supports for purifying human plasmatic immunoglobulins from Cohn II+III fraction," Biotech. Blood Proteins, 227: 207-212 (1993).
Nydegger, "Sepsis and Polyspecific Intravenous Immunoglobulins," J. Clin. Apheresis, 12: 93-99 (1997).
Office Action dated Jan. 4, 2011, for Canadian Patent Application No. 2,545,939 (3 pages).
Office Action, mailed Jun. 7, 2010, for U.S. Appl. No. 10/579,357.
Office Action, mailed Nov. 16, 2009, for U.S. Appl. No. 10/579,357.
Office Action, mailed Sep. 26, 2008, for U.S. Appl. No. 10/579,357.
Oldham et al., "A Quantitative Method for Measuring in vitro Synthesis of IgA and IgG by Human Rectal Mucosa: Studies on normal controls and patients with hypogammaglobulinemia," Immunol., 37: 661-668 (1979).
Opponent Grifols, S.A.'s response to Proprietor's Letter, filed Jun. 10, 2014, for European Patent No. 1687028 B1 (Application No. 04818790.0-1412) (20 pages).
Parkins et al., "The Formulation of Biopharmaceutical Products," Pharmaceutical Science & Technology Today, 3(4): 129-137 (2000).
Patent Owner's Response to Notice of Opposition submitted Mar. 7, 2014, for European Patent No. 1687028 B1 (Application No. 04818790.0-1412) (30 pages), including transmittal letter of Carpmaels & Ransford, submission list, observations, and main request claims (13 pages).
Patent owner's response to Notice of Opposition to European Patent 2 531 218 B1, submitted Feb. 12, 2020 (21 pages).
Wang, "Instability, stabilization, and formulation of liquid protein pharmaceuticals," Int. J. Pharmaceutics 185: 129-188 (1999).
Qi et al., "Characterization of the Photodegradation of a Human IgG1 Monoclonal Antibody Formulated as a High-concentration Liquid Dosage form," J. Pharm. Sci., 98(9): 3117-3130 (2009).
Rathore et al., "Current Perspectives on Stability of Protein Drug Products during Formulation, Fill and Finish Operations", Biotechnol. Prog. 24, pp. 504-514 (2008).
Record of Oral Hearing, mailed Jan. 24, 2014, for U.S. Appl. No. 10/579,357.
Wells et al., "Cord Serum IgA Levels in Australian Infants," J. Pediatrics Child Health, 16(3): 189-90 (1980) (Abstract).

"Human Normal Immunoglobulin For Intravenous Administration, Immunoglobulinum humanum normale ad usum intravenosum", Excerpt from European Pharmacopoeia, 1997:0918 (3 pages).
CSL Behring AG, Application for Inclusion of Polyvalent Human Immunoglobulins 20% for subcutaneous administration, in the WHO Model List of Essential Medicines and in the WHO Model List of Essential Medicines for Children, Hizintra® Fachinformation (Nov. 2012) (37 pages).
Li et al., "Chemical Instability of Protein Pharmaceuticals: Mechanisms of Oxidation and Strategies for Stabilization", Biotechnology and Bioengineering, 48, pp. 490-500 (1995).
Maggio, E. T., "Use of excipients to control aggregation in peptide and protein formulations", J. Excipients and Food Chem., 1(2), pp. 40-49 (2010).
Octagam-Infusionsflasche, Austria-Codex Fachinformation 1997/1998, Band 2 M-Z, pp. 2351-2352.
Octpharma Gammanorm Fachinformation (7 pages).
Opposition in corresponding EP Patent No. EP 3 226 895, issued Apr. 22, 2021 (36 pages).
Schott TopPac® Brochure, Polymer Prefillable Syringes (24 pages).
Schott TopPac® Polymer Prefillable Syringes Website (2021) (3 pages).
Schott TopPac® Polymer Prefillable Syringes Website Waybackmachine 2014 (2 pages).
Schott TopPac®, Polymer Prefillable Syringes, Brochure Waybackmachine 2013 (14 pages).
Strategic Development, Inspection, Safety & Regulatory Compliance and Commercialization of Pre-Filled Syringes, Pre-Filled Syringe-Forum 2008 (Jan. 17-18, 2008) (7 pages).
Yoshino et al., "Functional Evaluation and Characterization of a Newly Developed Silicone Oil-Free Prefillable Syringe System", Journal of Pharmaceutical Sciences, 103, pp. 1520-1528 (2014).
Buchacher, A. et al., "Anticomplementary activity of IVIG concentrates—important assay parameters and impact of IgG polymers", Vox Sanguinis (2010) 98:e209-e218.
Summary Basis for Regulatory Action; Grifols Therapeutics, Inc., GAMUNEX-C, Gammaked/Immune Globulin Injection (Human) 10% Caprylate/Chromatography Purified, Nov. 9, 2015, 8 pages.
Summary Basis for Regulatory Action; Grifols Therapeutics, Inc., Immune Globulin Subcutaneous, Human—klhw, 20%, XEMBIFY Jul. 3, 2019, 12 pages.
Summary Basis for Regulatory Action; Octapharma Pharmazeutika Produktionsges.m.b.H., CUTAQUIG/Immune Globulin Subcutaneous (Human), Dec. 12, 2018, 14 pages.
Highlights of Prescribing Information: CUTAQUIG (Immune Globulin Subcutaneous (Human)—hipp), 16.5% solution, 2018, 28 pages.
Highlights of Prescribing Information: CUVITRU (Immune Globulin Subcutaneous (Human, 20% solution, 2016, 30 pages.
Highlights of Prescribing Information: XEMBIFY (Immune Globulin Subcutaneous, human—klhw) 20% solution, 2019, 31 pages.
Highlights of Prescribing Information: GAMMAGARD Liquid, Immune Globulin Infusion (Human), 10% Solution, for intravenous and subcutaneous administration, 2005, 37 pages.
Highlights of Prescribing Information: GAMUNEX-C, [Immune Globulin Injection (Human), 10% Caprylate/Chromatography Purified], 2003, 53 pages.
Highlights of Prescribing Information: HYQVIA [Immunte Globulin Infusion 10% (Human) with Recombinant Human Hyaluronidase] Solution, for subcutaneous administration, 2014, 40 pages.
Department of Health and Human Services, Center for Biologics Evaluation and Research, Baxalta U.S. Incorporated, Final CMC review of Baxalta U.S. Incorporated's IGSC (GAMMAGARD Liquid), Jun. 29, 2016, 10 pages.

* cited by examiner

PHARMACEUTICAL PRODUCT WITH INCREASED STABILITY COMPRISING IMMUNOGLOBULINS

This application is a national stage filing under 35 U.S.C. § 371 of International Application No. PCT/EP2015/078482, filed Dec. 3, 2015, which claims priority of European Patent Application No. 14196069.0, filed Dec. 3, 2014. The contents of these applications are each incorporated herein by reference.

BACKGROUND OF THE INVENTION

Primary immunodeficiency (PID) disorders, such as common variable immunodeficiency (CVID) and X-linked agammaglobulinemia, predispose patients to recurrent infections. These patients require immunoglobulin (Ig) replacement therapy, which can be administered intravenously (IVIg) or subcutaneously (SCIg). Immunoglobulin therapy with IVIg or SCIg has also been shown to be useful in the treatment of other conditions, for example in the treatment of inflammatory and autoimmune conditions, as well as certain neurological disorders. In addition, there are other products containing polyclonal immunoglobulins enriched in certain immunoglobulin specificities, for example immunoglobulin enriched in anti-cytomegalovirus antibodies, such as Cytogam™, or immunoglobulin enriched in anti-D antibodies such as Rhophylac™, which are administered by intravenous injection, or, for Rhophylac, by intravenous or intramuscular injection.

If immunoglobulin is administered via the more common intravenous route, a sharp rise in serum immunoglobulin level is produced which declines as Ig redistributes into the extravascular space over the next 48 hours, and then falls with first-order kinetics over approximately three weeks before intravenous administration is repeated. Many patients report feeling a "wear-off"-effect during the last week of the dosing interval, in particular malaise, fatigue, arthralgias, myalgias or increased susceptibility to infections.

Considering the drawbacks of intravenous Ig administration, Ig administration via the subcutaneous route has become increasingly popular in recent years. The method does not require venous access, is associated with only few systemic side effects and has been reported to improve patient's quality of life.

One of the challenges in the formulation of an Ig preparation, and in particular of an Ig preparation for subcutaneous administration, lies in the fact that Ig dissolved in aqueous solution tend to aggregate and form precipitates. A further challenge is the long-term stability of Ig preparations when stored in solution.

In order to achieve a sufficient stability and avoid adverse effects on the quality of the product, Ig preparations are usually stored in glass vials that are closed with a sterile rubber stopper and a cap, e.g. an aluminium lid. In order to increase the stability of the solution, inert gassing can be applied to the vial prior to closing the vial with a rubber stopper, as disclosed in WO 2011/104315. The product is typically withdrawn from the vial by pushing the needle of a syringe or a plastic spike through the rubber stopper and soaking the solution into the syringe barrel.

While excellent stability has been achieved with such preparations, it is desirable to further increase the stability and convenience of use of a highly concentrated Ig solution. As is well known, and has been used for therapeutic proteins including polyclonal and monoclonal antibodies for some years, the convenience can be increased by using pre-filled syringes, which eliminates the cumbersome step of drawing the solution into a syringe. For example, polyclonal IgG products Rhophylac™ and Beriglobin™ have been sold in pre-filled syringes for many years, as have monoclonal IgG products such as Enbrel™. Traditionally glass syringes were used, but the availability of a variety of suitable polymer syringes makes it very feasible to switch to polymer syringes for protein products, and the trend in the industry is towards increasing use of polymer pre-filled syringes. In WO2012022734, pre-filled syringes, including polymer syringes, are disclosed for a monoclonal antibody. WO2014041307 also discloses immunoglobulin solutions in pre-filled syringes. Stability was investigated for up to 12 months; a kit where the pre-filled syringe is sealed hermetically is included, but the use of oxygen scavengers is not contemplated.

To find a system with increased stability and increased convenience to the user, be it patient or health care professional, the inventors have investigated the stability of a highly concentrated Ig product pre-filled in polymer syringes, comprised in air-tight packaging including an oxygen scavenger. Surprisingly, the inventors have found that such a product has even superior stability than the same solution stored in glass vials, even with inert gassing being applied prior to stoppering.

SUMMARY OF THE INVENTION

The inventors have found that Ig solutions can be stored in polymer syringes, packaged air-tight with an oxygen scavenger, for at least 18 months with no adverse effect on product quality. Surprisingly, the stability of the immunoglobulin solution stored like this is even better than in glass vials with inert gassing. The polymer syringes may be ready-to-use so that no separate filling step is necessary for the patient or health care professional to transfer the solution into a syringe which is eventually used for administering the Ig preparation to the patient. Even in cases where the patient or health care professional may need to transfer the solution to a different syringe or other container that fits on a pump, the cumbersome step of drawing the solution into a syringe from a vial is eliminated, and the solution can easily and conveniently be transferred from one syringe to another via a simple connector. Therefore, the pre-filled polymer syringes provide much increased convenience to the patient. In addition, polymer syringes are safer for handling, as they are more resistant to mechanical damage.

The present invention therefore relates to the following subject matter defined in items (1) to (32):

(1) A pharmaceutical product comprising a polyclonal or monoclonal immunoglobulin solution in a pre-filled polymer syringe, comprised in air-tight packaging comprising an oxygen scavenger. Preferably the air-tight packaging is a blister pack.

(2) The pharmaceutical product of item (1), wherein the immunoglobulin solution is to be administered intravenously or subcutaneously.

(3) The pharmaceutical product of item (1) or item (2), wherein the immunoglobulin solution comprises at least 5% (w/v) IgG.

(4) The pharmaceutical product of any previous item, wherein the immunoglobulin solution comprises IgG that is at least 95% pure.

(5) The pharmaceutical product of any previous item, wherein the immunoglobulin solution is formulated with a stabilizer.

(6) The pharmaceutical product of any previous item, wherein the volume of the immunoglobulin solution in the syringe is 1 ml or more.

(7) The pharmaceutical product of any previous item, wherein the polymer syringe is made of or comprises a cycloolefin copolymer, a cycloolefin polymer, or a combination thereof.

(8) The pharmaceutical product of any of items (1) to (6), wherein the polymer syringe is made of or comprises a polypropylene, a polyethylene, a polyacryl, or a polystyrene or combinations thereof.

(9) The pharmaceutical product of any previous item, wherein the inside of the syringe is coated prior to filling it, e.g. wherein the inside of the syringe is siliconized.

(10) The pharmaceutical product of any of items (1) to (8), wherein the inside of the syringe is not coated; in such a syringe, the plunger may be treated to increase its slidability inside the syringe, e.g. by coating the plunger with a material to increase its slidability such as Polytetrafluorethylene (PTFE).

(11) The pharmaceutical product of any previous item, wherein the headspace is less than 20% of the volume of the immunoglobulin solution.

(12) The pharmaceutical product of any previous item, wherein the air-tight packaging is a blister pack or a sealed multilayer foil bag.

(13) The pharmaceutical product of any previous item, wherein the oxygen scavenger comprises a metal oxide or a polymer resin.

(14) The pharmaceutical product of any previous item, wherein the air-tight packaging has been filled with inert gas.

(15) The pharmaceutical product of any of items (1) to (13), wherein air-tight packaging has not been filled with inert gas.

(16) The pharmaceutical product of any previous item, wherein the immunoglobulin solution is protected from light, optionally by additional packaging.

(17) The pharmaceutical product of any previous item, wherein the syringe is suitable for insertion or attachment to a catheter, a syringe driver, any pumping device, or an autoinjector.

(18) The pharmaceutical product of any previous item, wherein the syringe has a standard luer lock.

(19) The pharmaceutical product of any previous item, wherein the syringe is suitable for transferring the product directly or via tip-to-tip connector to the reservoir of an infusion pump or an autoinjector, or to another syringe suitable for a syringe pump or syringe driver.

(20) The pharmaceutical product of any one of the previous items, wherein a needle is attached to the syringe; preferably the needle is a 20 to 30 Gauge needle, more preferably a 25 to 30 Gauge needle.

(21) The pharmaceutical product of any one of the preceding items, wherein the immunoglobulin solution is stable over a period of at least 18 months.

(22) The pharmaceutical product of any one of the preceding items, wherein the immunoglobulin solution is stable over a period of at least 30 months, preferably at least 36 months.

(23) A kit comprising a pre-filled polymer syringe comprising a polyclonal or monoclonal immunoglobulin solution comprised in air-tight packaging comprising an oxygen scavenger; a 20 to 30 Gauge needle provided separately or inside the air-tight packaging; a mounted plunger rod or a non-mounted plunger rod (i.e. a plunger rod that can reversibly attach to the plunger in the syringe), which may be provided separately or inside the air-tight packaging. Preferably, the needle is supplied in a sterile blister pack, which may be provided within or separate from the air-tight packaging.

(24) A method of producing the product of any previous item, wherein the stopper in the syringe is applied with a positioning rod or a vacuum stoppering technique.

(25) The use of a polymer syringe in air-tight packaging including an oxygen scavenger for long-term storage of a polyclonal immunoglobulin composition.

(26) The use of a pharmaceutical product as defined in any one of items (1)-(22) for long-term storage of a polyclonal immunoglobulin composition.

(27) The use of item (25) or (26), wherein the long-term storage is storage over a period of at least 18 months, preferably of at least 30 months, even more preferably of at least 36 months.

(28) A pharmaceutical product as defined in any one of items (1)-(22) or a kit of item (23) for use in the treatment of an immunodeficiency disorder.

(29) The pharmaceutical product or kit for use according to item (28), wherein the immunodeficiency disorder is a primary immunodeficiency disorder.

(30) The pharmaceutical product as defined in any one of items (1) to (22) or the kit of item (23), for use in the treatment of an autoimmune disorder or a neurological disorder.

(31) The pharmaceutical product or kit for use according to item (30), wherein the autoimmune or neurological disorder is Rheumatoid arthritis, Systemic Lupus Erythematosus (SLE), Antiphospholipid syndrome, immune thrombocytopenia (ITP), Kawasaki disease, Guillain Barré syndrome (GBS), multiple sclerosis (MS), chronic inflammatory demyelinating polyneuropathy (CIDP), multifocal motor neuropathy (MMN), myasthenia gravis (MG), skin blistering diseases, scleroderma, Dermatomyositis, Polymyositis, Alzheimer's Disease, Parkinson's Disease, Alzheimer's Disease related to Downs Syndrome, cerebral amyloid angiopathy, Dementia with Lewy bodies, Fronto-temporal lobar degeneration or vascular dementia.

(32) Use of an oxygen scavenger comprised in an air-tight packaging with a pre-filled polymer syringe comprising an immunoglobulin solution to increase the storage stability of the immunoglobulin solution.

DETAILED DESCRIPTION

Figure 1:
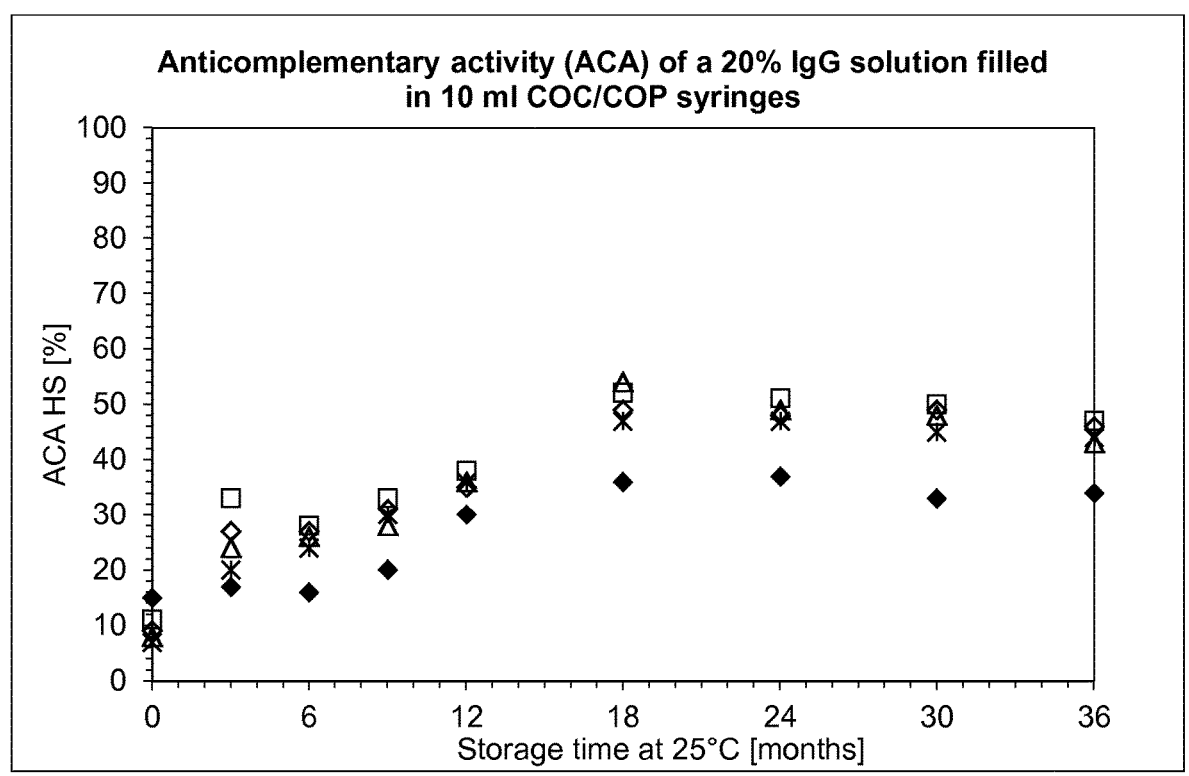
FIG. 1: Anticomplementary activity (ACA) of a 20% IgG solution filled in 10 ml COC/COP syringes stored protected from light without blister. □ BD Sterifill SCF syringes * Terumo Plajex syringes Δ Daikyo Rezin CZ ◇ Schott TopPac ◆ Reference filling in glass vials
Figure 2:
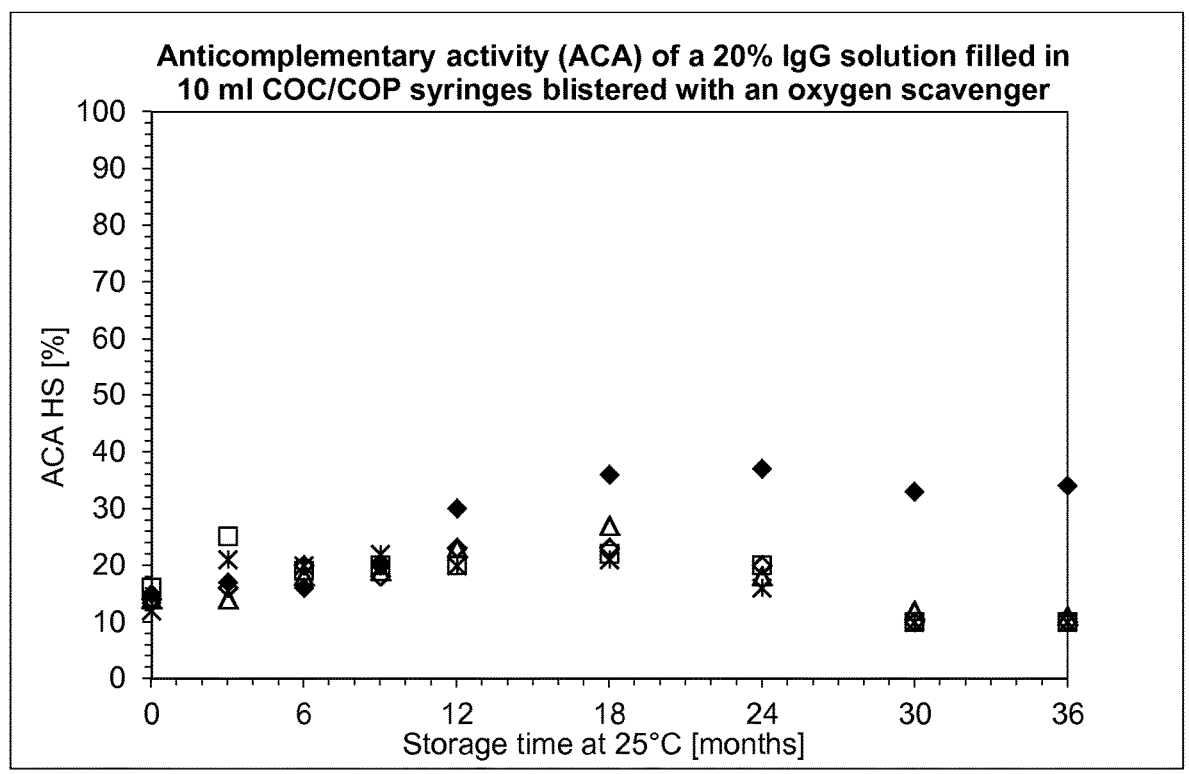
FIG. 2: ACA of a 20% IgG solution filled in 10 ml COC/COP syringes blistered with an oxygen scavenger. □ BD Sterifill SCF syringes * Terumo Plajex syringes Δ Daikyo Rezin CZ ◇ Schott TopPac ◆ Reference filling in glass vials
Figure 3:
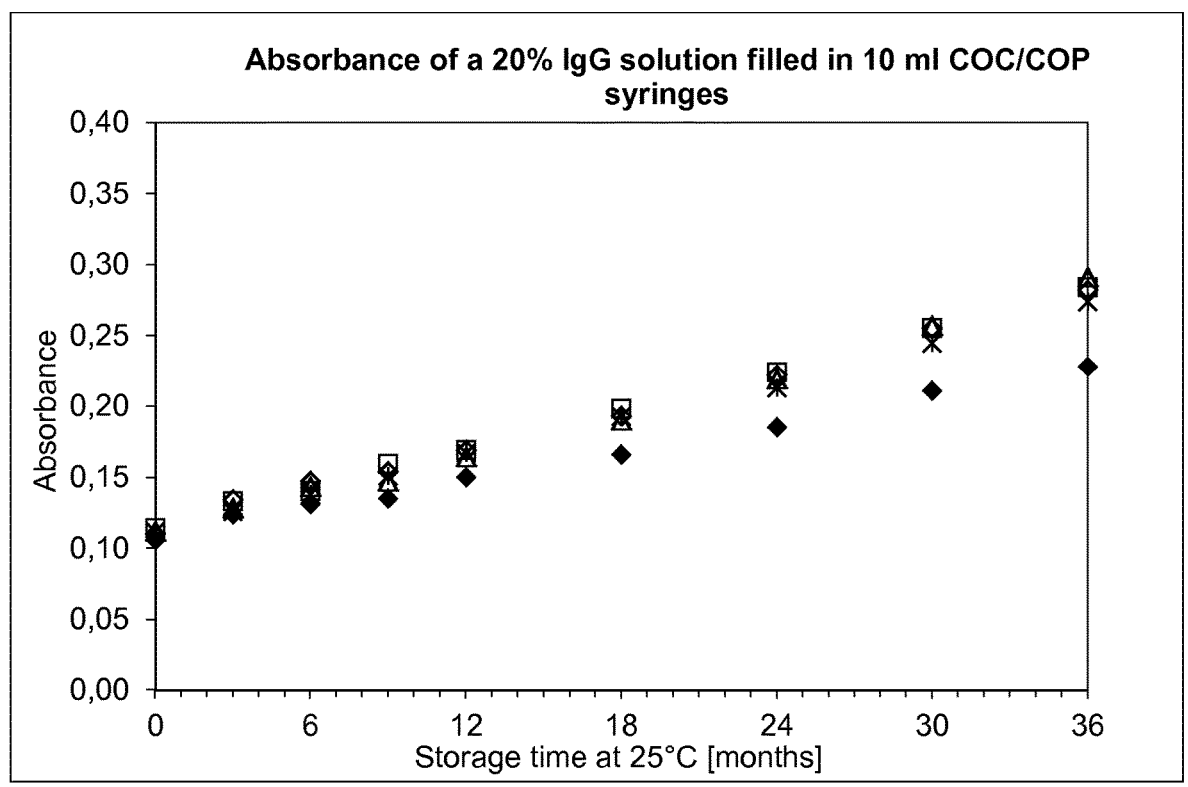
FIG. 3: Absorbance of a 20% IgG solution filled in 10 ml COC/COP syringes stored protected from light without blister. □ BD Sterifill SCF syringes * Terumo Plajex syringes Δ Daikyo Rezin CZ ◇ Schott TopPac ◆ Reference filling in glass vials

The present invention relates to a pharmaceutical product comprising an immunoglobulin solution in a pre-filled polymer syringe, comprised in air-tight packaging including an oxygen scavenger. The pharmaceutical product may be ready-to-use, i.e. it can be directly applied to the patient without additional transfer steps or processing steps such as dilution or reconstitution. Alternatively, the immunoglobulin solution can be easily transferred from pre-filled syringe into a special syringe or container, when a special syringe or container is required for application, e.g. in a pump system.
The Immunoglobulin Solution The immunoglobulin solution may contain monoclonal or polyclonal immunoglobulin(s). Preferably, the immunoglobulin(s) contained in the immunoglobulin solution are polyclonal. The immunoglobulin may be an antibody or a fragment thereof. Preferably, the Ig solution comprises IgG and/or other isotypes such IgA and IgM. In one embodiment, the immunoglobulins in the Ig solution essentially consist of IgG. In another embodiment, the immunoglobulins in the Ig solution essentially consist of IgA, or a mixture of IgA and IgM. In another embodiment, the immunoglobulins in the Ig solution may be a mixture of IgG, IgA and IgM.

The immunoglobulins can be isolated from human or animal blood or produced by other means, for instance by recombinant DNA technology or hybridoma technology. In preferred embodiments, immunoglobulins are obtained from blood plasma, typically from a pool of blood plasma from many donors. In order to obtain the immunoglobulins from plasma, the plasma is usually subjected to alcohol fractionation, which may be combined with other purification techniques like chromatography, adsorption or precipitation. However, other processes can also be used.

The solution can be formulated by methods known in the art. In the case of an IgG solution, the pH of the final preparation may be adjusted to a relatively high but acidic pH, namely in the range of about pH 4.2 to 5.4. It has been found that this pH range is particularly useful for improving the storage of characteristics of polyclonal immunoglobulin G preparations.

The pH range is preferably from 4.5 to about 5.2, a pH range of about 4.6 to 5.0 being particularly preferred, pH 4.8 being especially preferred. In the case of IgA, or a combination of IgA and IgM, a more neutral pH may be preferable.

In a preferred embodiment the Ig solution comprises immunoglobulins of different specificities. In another preferred embodiment, the Ig solution comprises immunoglobulins of different specificities, wherein certain immunoglobulins specific for certain antigens have been enriched relative to normal Ig preparation from healthy individuals.

The Ig solution preferably comprises a stabilizer. Preferably, the Ig solution comprises one or more amino acids as stabilisers; preferably, the amino acids are selected from the group consisting of non-polar and basic amino acids. Exemplary non-polar and basic amino acids, useful for the purposes of the present invention are histidine, arginine, lysine, ornithine (basic amino acids) and isoleucine, valine, methionine, glycine and proline (non-polar amino acids). Particularly useful is proline. The stabilizer may be an amino acid of the group of non-polar or basic amino acids on its own, or it may be a combination of 2 or more such amino acids. The amino acid stabilizers may be natural amino acids, amino acid analogues, modified amino acids or amino acid equivalents. L-amino acids are preferred. When proline is used as the stabiliser, it is preferably L-proline. It is also possible to use proline equivalents, e.g. proline analogues. The amount of proline in the immunoglobulin solution preferably ranges from about 10 to about 2000 mmol/l, more preferably from about 50 to about 1000 mmol/l, even more preferably from about 100 to 500 mmol/l, and most preferably is about 250 mmol/l.

Preferably, the stabilizer is present in the Ig solution at a concentration of at least 0.2 M. More preferably, the final concentration is between 0.2 M and 0.4 M, more preferably between 0.2 M and 0.3 M, most preferably 0.25 M.

The Ig solution preferably has a protein concentration of about 5 to 35% w/v, more preferably about 10 to 30% w/v, still more preferably about 15 to 30% w/v, most preferably about 18 to 25% w/v, e.g. 20% w/v. The final protein concentration will depend on various factors, such as the administration route, the type of condition to be treated, etc. The skilled person will be able to determine the optimal protein concentration for the intended application. For example, for intravenous infusion, the final preparation of the invention preferably has a protein concentration of about 5 to 15% w/v, preferably about 8 to 12% w/v, for example 5%, 6%, 7%, 8%, 9%, 10%, 11%, 12%, 13%, 14% or 15%. In the case of IgG for intravenous use, 10% w/v, i.e. 100 g IgG/litre is particularly useful. For subcutaneous administration a higher concentration may be chosen, for instance about 15 to 35% w/v, most preferably about 20 to 30% w/v, for example 16%, 17%, 18%, 19%, 20%, 21%, 22%, 23%, 24%, 25%, 26%, 27%, 28%, 29% or 30%. For hyperimmune preparations, e.g. Cytogam™ or Rhophylac™, smaller concentrations may be favoured. For example, the concentration could be between 0.5 and 6%, between 1 and 5%, between 1 and 3%, for example around 1.5%.

The IgG content in the Ig solution is preferably at least 95% (w/w), preferably at least 96% (w/w), more preferably at least 97% (w/w), more preferably at least 98% (w/w), referred to the total amount of protein in the Ig solution.

For IgA solutions, the IgA content in the Ig solution is preferably at least 50% (w/w), more preferably at least 60% (w/w), even more preferably at least 70% (w/w), most preferably at least 80% (w/w). The IgA solutions may contain mostly monomeric IgA, it may contain the same ratio of monomeric to dimeric/polymeric IgA as found in plasma, or it may be enriched in dimeric IgA, and it may also comprise secretory component.

For combined IgA and IgM solutions, the IgA and IgM content is at least 50% (w/w), preferably at least 60% (w/w), more preferably at least 70% (w/w), even more preferably at least 80% (w/w), most preferably at least 90% (w/w). In such a preparation, the IgA is preferably enriched in dimeric IgA. The solution may also comprise secretory component.

The Ig solution may further comprise one or more pharmaceutically acceptable additives. Such additives can be excipients, and other substances such as non-buffering substances, for example sodium chloride, glycine, sucrose, maltose and sorbitol. Such pharmaceutical compositions may be administered via various routes. For intravenous administration, a dosage of about 0.2 g, preferably 0.5 g to about 2.0 g of immunoglobulin/kilogram of body weight per day may be used.

In the most preferred embodiment, the Ig solution comprises Human normal immunoglobulin, wherein 1 ml of the solution contains 200 mg/ml human plasma protein, with at least 98% IgG and an IgA content of less than 0.05 mg/ml. The approximate distribution of the IgG subclasses will typically resemble about the average subclass distribution in human plasma. In a typical preparation the approximate subtype distribution is:

IgG1 . . . 62-74%
IgG2 . . . 22-34%
IgG3 . . . 2-5%
IgG4 . . . 1-3%.

In this embodiment, the solution further comprises the following excipients: L-proline, Polysorbate 80, and water for injections.

The Ig solution in the pharmaceutical product of the present invention has excellent stability. Preferably, the Ig solution shows no substantial difference to a control Ig solution which has been stored in a glass vial for the same period of time under the same conditions, with respect to the following parameters:

Molecular size distribution, as determined by size-exclusion HPLC
Density, determined by a digital densitometer according to EP or USP method
pH (1% protein solution)
Fc Function (Human blood red cell test (complement mediated hemolysis) according to the European Pharmacopoiea (EP)).
Prekallikrein activator (PKA), based on the determination of the kallikrein activity according to EP
Anti-Streptolysin-0 Antibody Content: The anti-Streptolysin-0 antibody (ASL-0) content is determined by nephelometry.
Hepatitis B Antibody titer (HBs): The test for the quantitative determination of anti-HBs is a commercially available one-step solid phase enzyme immunoassay (EIA), based on the sandwich principle.
Protein purity The period of time assessed is preferably at least 6 months, more preferably at least 12 months, more preferably at least 18 months, more preferably at least 24 months, even more preferably at least 30 months, most preferably 36 months or longer.

Preferably, at least two of the above-recited parameters are unchanged relative to the control solution, more preferably at least 3 or at least 4, or at least 5, or at least 6, or at least 7. Most preferably all of the above-recited parameters are unchanged relative to the control solution.

In certain embodiments, the Ig solution in the pharmaceutical product of the present invention is superior to a control Ig solution which has been stored in a glass vial for the same period of time under the same conditions, with respect to the following parameters:

Coloration, determined by UV/VIS extinction measurement at 350/500 nm (see examples)
Anticomplementary Activity (ACA): Anticomplementary activity is determined in a hemolysis system using sensitized sheep erythrocytes and human serum as complement source (ACA HS), see examples.

For example, the absorbance of the Ig solution in the pharmaceutical product of the present invention at 350 nm may be lower than that of a control solution in a glass vial, after storage for 18, 24, 30 or even 36 months under identical conditions.

The ACA of the Ig solution in the pharmaceutical product of the present invention may be lower than that of a control solution in a glass vial, after storage for 18, 24, 30 or even 36 months under identical conditions.

The Syringe

The "polymer syringe" of the present invention typically has a barrel being made of polymer material and a plunger including a sliding plug tightly contacting with the inner surface of the barrel. At one end, the barrel has a cap or an injection needle. At the opposite end, the barrel has an open end, and the plunger is inserted into the open end. The syringe may also have means for preventing undesired withdrawal of the plunger from the barrel. Such means are known to those of skill in the art.

At least the barrel is made of polymer. Preferably, also the plunger is made of polymer. The syringe may be made of different polymer materials. The polymer material of the barrel is preferably transparent.

Preferably, a plunger rod is also included, which may be supplied already attached to the plunger or may be supplied separately and can be attached to the plunger by the user, e.g. by screwing the plunger rod into the plunger. The plunger rod may be provided within the air-tight packaging or may be supplied separately. Preferably, the plunger rod is also made of polymer material, which may be the same or different from the polymer material that the barrel is made of.

As used herein, the term "polymer" or "polymer material" refers to a macromolecule composed of many repeating subunits. The polymer may comprise only one type of subunit or monomer (homopolymer), or may comprise two or more different subunits (copolymer). The term denotes a synthetic or semi-synthetic polymer. Preferably, the polymer is selected from the group consisting of polyolefins, acrylic polymers, fluorinated polymers, diene polymers, vinyl copolymers, aldehyde condensation polymers, cellulosics, polyamides, polyesters, polyethers, polyimides, polysulfides, cyclic olefin polymers, and cyclic olefin copolymers.

In one embodiment, the polymer material is a polyolefin selected from the group consisting of polyethylene, polypropylene, polystyrene, polyvinyl chloride, polyvinylidene chloride and polyvinyl acetate.

In another embodiment, the polymer material is an acrylic polymer selected from the group consisting of polyacrylonitrile, polymethyl methacrylate, polymethyl acrylate, polyethyl acrylate and polyacrylate elastomers.

In another embodiment, the polymer material is a fluorinated polymer selected from the group consisting of polytetrafluoroethylene, fluoroelastomers, polyvinyl fluoride and polyvinylidene fluoride.

In another embodiment, the polymer material is a diene polymer selected from the group consisting of polybutadiene, polychloroprene, and polyisoprene.

In another embodiment, the polymer material is a vinyl copolymer selected from the group consisting of acrylonitrilebutadiene-styrene, styrene-butadiene rubber, styrene-acrylonitrile, nitrile rubber, butyl rubber, styrene-butadiene and styrene-isoprene block copolymers, ethylene-propylene copolymers and styrene-maleic anhydride copolymer.

In another embodiment, the polymer material is an aldehyde condensation polymer selected from the group consisting of phenol formaldehyde, urea-formaldehyde polymers and melamine-formaldehyde polymers.

In another embodiment, the polymer material is a cellulosic polymer selected from the group consisting of rayon, cellulose nitrate and cellulose acetate.

In another embodiment, the polymer material is a polyamides selected from the group consisting of Nylon and aramids.

In another embodiment, the polymer material is a polyester selected from the group consisting of polyethylene terephthalate, polybutylene terephthalate, polycarbonate, degradable polyesters, alkyds and unsaturated polyesters.

In another embodiment, the polymer material is a polyether selected from the group consisting of polyacetal, polyphenylene oxide, polyetherketone, polyetheretherketone, and aliphatic polyethers.

In another embodiment, the polymer material is a polyimide selected from the group consisting of polyamideimide and polyetherimide.

Most preferably, the polymer material is a cyclic olefin polymer (COP) or a cyclic olefin copolymer (COC). These polymers are known per se, see, e.g., IUPAC technical report, Pure Appl. Chem., Vol. 77, No. 5, pp. 801-814, 2005.

The inner wall of the barrel of the syringe may be used uncoated, or may be coated, e.g. with a silicone-containing material. The silicone-containing material is preferably selected from the group consisting of polydimethyl siloxane, e.g. dimethyldiphenylpolysiloxane copolymers, dimethyl, methylphenylpolysiloxane copolymers, polymethylphenylsiloxane, and methylphenyl, dimethylsiloxane copolymers. If the inner wall of the barrel of the syringe is used uncoated, the plunger may be treated to increase its slidability, e.g. by coating it with a fluorinated polymer material such as PTFE.

The nominal volume of the syringe may range from 1 ml to 150 ml, preferably from 2 ml to 125 ml, more preferably from 3 ml to 100 ml, more preferably from 4 ml to 750 ml, or from 5 ml to 50 ml. Preferably the nominal volume of the syringe is 1 ml, 2 ml, 2.25 ml, 2.5 ml, 3 ml, 4 ml, 5 ml, 10 ml, 15 ml, 20 ml, 30 ml, 40 ml, 50 ml, 75 ml, 100 ml, 125 ml, or 150 ml.

The volume of the Ig solution within the pre-filled syringe may range from 1 ml to 120 ml, preferably from 2 ml to 100 ml, more preferably from 3 ml to 80 ml, more preferably from 4 ml to 60 ml, or from 5 ml to 50 ml. Preferably the volume of the Ig solution within the prefilled syringe is 1 ml, 2 ml, 3 ml, 4 ml, 5 ml, 10 ml, 15 ml, 20 ml, 30 ml, 40 ml, 50 ml or 100 ml.

Typically there will be a headspace within the pre-filled syringe. The term "headspace" refers to a gaseous layer above the solution within the syringe. The volume of the headspace within the pre-filled syringe is typically less than 30% of the volume of the Ig solution, preferably less than 25%, more preferably less than 20%, even more preferably it is less than 15%, most preferably less than 10%, for example between 5 and 10%%. Expressed differently, the headspace in smaller syringes (5 ml or less) is typically around 2 to 3 mm of the syringe barrel, in larger syringes about 3 to 5 mm. However, the head space can be further reduced by using the vacuum stoppering technique.

In particular, the pre-filled syringe in air-tight packaging comprising an oxygen scavenger of the invention provides a good stability of an Ig preparation after a prolonged storage period of 18 or 24 months, even of 30 or even 36 months, at room temperature in the dark. When using a 20% Ig preparation as reference, the pre-filled syringe in air-tight packaging comprising an oxygen scavenger of the invention provides that the absorbance $A_{350-500\ nm}$ of the immunoglobulin solution remains below 0.15 upon storage for 24 months at 25° C. in the dark, preferably the absorbance $A_{350-500\ nm}$ remains below 0.15 even after storage for 36 months. The pre-filled syringe in blister packs comprising an oxygen scavenger of the invention provides a stable immunoglobulin preparation showing an increase in $A_{350-500\ nm}$ of less than 0.1, preferably of less than 0.08, even more preferably of less than 0.05, most preferably less than 0.02, when stored at 25° C. in the dark for 36 months.

When using a 20% Ig preparation as reference, the pre-filled syringe in air-tight packaging comprising an oxygen scavenger of the invention provides that the ACA of the immunoglobulin solution remains below 25%, preferably below 20%, more preferably below 18%, upon storage for 24 months at 25° C. in the dark, preferably the ACA remains below 25%, preferably below 20%, even more preferably below 15% even after storage for 36 months. The pre-filled syringe in air-tight packaging comprising an oxygen scavenger of the invention provides a stable immunoglobulin preparation showing an increase in ACA of less than 0.1, preferably of less than 0.08, even more preferably of less than 0.05, most preferably less than 0.02, when stored at 25° C. in the dark for 36 months.

The pre-filled syringe may be supplied with a needle attached, preferably a hypodermic needle. The needle can have various gauge values. The gauge value of the needle may range from 18 to 35 G, preferably from 20 to 30 G. The preferred gauge value of the needle will vary depending on the intended route of administration. For example, for intramuscular administration 18 to 21 G is preferred, for intravenous administration, 23 to 25 G is preferred, whereas for subcutaneous administration, 25 to 30 G is preferred, more preferably 25 to 29 G, most preferably 27 to 29 G. For intramuscular administration, 20 to 22 G needles may be preferred.

Alternatively, the needle may be supplied separate from the pre-filled syringe, but supplied with the syringe as, for example, a kit. For example, the pre-filled syringe in air-tight packaging with an oxygen scavenger may be packaged with a separate needle in further packaging. The plunger rod may also be supplied detached from the plunger, as part of the kit. All components of the kit may be supplied within the air-tight packaging, or packaged separately.

Secondary Packaging

The pharmaceutical product of the invention comprises a secondary packaging, wherein the pre-filled syringe is within the secondary packaging. The secondary packaging is preferably a blister pack; alternatively it may be a sealed pouch. Other options for air-tight secondary packaging are also envisaged. The secondary packaging, preferably the blister pack, is preferably made of an oxygen-impermeable material, also referred to as "air-tight" herein. The term "oxygen-impermeable" or "air-tight" refers to a material that provides a barrier for oxygen, such that the oxygen transmission rate for the unformed material is lower than 5 $cm^3/m^2$ per day measured according to DIN 53380 at a pressure of 1 bar, a temperature of 23° C., and relative humidity of 35%. Preferably, the oxygen transmission rate is lower than 3 $cm^3/m^2$ per day, more preferably lower than 2 $cm^3/m^2$ per day, even more preferably about or less than 1 $cm^3/m^2$ per day. The material may be a polymer. Suitable polymers for use in the present invention include any thermoplastic homopolymer or copolymer. Examples of polymers include, but are not limited to, polyethylene terephthalate (un-oriented PET, oriented PET or PETG), polyethylene naphthalate (PEN), polyethylene naphthalate copolymers (e.g., PEN blended with PET at a ratio of about 10% to 25%), nylon, polyvinyl chloride, polyvinylidene chloride, polytetrafluroethylene, polypropylene, polystyrenes, polycarbonates, ethylene copolymers (such as ethylene-vinyl acetate, ethylene-alkyl acrylates or methacrylates, ethyleneacrylic acid or methacrylic acid, ethylene-acrylic or methacrylic acid ionomers) polyamides (such as nylon 6, nylon 66 and nylon 612) polybutylene terephthalate, polytrimethylene terephthalate, polyvinylidene dichloride, polyacrylamide, polyacrylonitrile, polyvinyl acetate, polyacrylic acid, polyvinyl methyl ether, polyethylene, polypropylene, ethylene-propylene copolymers, poly(1-hexene), poly(4-methyl-1 pentene), poly(1-butene), poly(3-methyl-1-butene), poly(3-phenyl-1-propene), poly(vinylcyclohexane) and any other suitable polymer to accomplish the objectives of the present invention. Blends of different polymers may also be used. Alternatively, materials such as foils, or a combination of the above mentioned materials with a foil, e.g. aluminium foil, may be used.

The secondary packaging comprises an oxygen scavenger. The term "oxygen scavenger", as used herein, means a material or chemical compound which can remove oxygen from the interior of a closed packaging by reacting or combining with entrapped oxygen or with oxygen that is leaking into the packaging interior after the packaging has been sealed or with oxygen leaking from the Ig solution in the syringe; or which can prevent or reduce the perfusion of oxygen through the packaging materials.

The oxygen scavenger can be contained in the interior of the secondary packaging, for example it may be contained in a sachet or other porous container. Alternatively it can be incorporated in the material of the primary or the secondary packaging itself, or as a coating on the surface of the primary or secondary packaging, or combinations of any or all of the above. For example, an oxygen scavenger can be incorporated in the polymer material of the syringe, e.g. COC multilayer syringes from Mitsubishi Gas Chemical. One oxygen scavenger or a combination of two or more oxygen scavengers may be used.

Based on the chemical mechanisms of active oxygen scavengers, they can be classified into the following categories (M. L. Rooney, Active Food Packaging, Blackie Academic & Professional, 1st Ed. 1995):

- inorganic oxygen scavengers, for example metal powder
- ascorbic acid based scavengers
- enzymatic scavengers
- polymer based oxygen scavengers For example, oxygen-scavenging materials may comprise an oxygen-scavenging element selected from calcium, magnesium, scandium, titanium, vanadium, chromium, manganese, iron, cobalt, nickel, copper, zinc, silver, tin, aluminium, antimony, germanium, silicon, lead, cadmium, rhodium, combinations thereof and any other materials suitable for effectively scavenging oxygen during container storage when necessary, so that immunoglobulins are not adversely effected in the pharmaceutical product of the present invention.

More preferably, the oxygen-scavenging materials comprise an oxygen-scavenging element selected from, for instance, calcium, magnesium, titanium, vanadium, manganese, iron, cobalt, nickel, copper, zinc, and tin. It will be understood that these oxygen-scavenging elements may be present as mixtures, in compounds such as oxides and salts, or otherwise combined with other elements, with the proviso that the oxygen-scavenging elements are capable of reacting with molecular oxygen. Metal alloys comprising at least one oxygen-scavenging element may also be suitable.

By way of illustration consistent with the present invention, an oxygen-scavenging packaging wall may be prepared by incorporating an inorganic powder and/or salt. The powder may be a reduced metal powder, such as reduced iron powder.

In one preferred embodiment of the invention, an oxygen scavenger in the package wall is combined with a transition-metal salt to catalyze the oxygen scavenging properties of the polymeric materials. Useful catalysts include those which can readily interconvert between at least two oxidation states. See Sheldon, R. A.; Kochi, J. K.; "Metal-Catalyzed Oxidations of Organic Compounds" Academic Press, New York 1981.

Polymer based oxygen scavengers consist of high molecular, ethylenically unsaturated hydrocarbons. An activation step often enables the user to start the oxygen scavenging when desired. Polymer based oxygen absorbers are offered by Mitsubishi Gas Chemical, Chevron Phillips, Southcorp Packaging, Cryovac and Honeywell. Polymer-based scavengers are preferred in accordance with this invention.

In certain embodiments, there is gas in the headspace of the syringe. The gas may have a reduced oxygen content compared to the surrounding air. However, in the present invention, even without reducing the amount of oxygen in the headspace prior/during the filling and stoppering, the oxygen concentration dissolved in the Ig preparation will typically become lower during storage, so it will be at a concentration below 200 µmol/l soon after the filling process, and then be preferably below 175 µmol/l, more preferably below 150 µmol/l, even more preferably below 125 µmol/l, and most preferably below 100 µmol/l over a prolonged storage period. Yellowish coloration upon long-term storage can be thus significantly reduced when the Ig preparation is stored at room temperature.

Methods for determining the oxygen content in a gaseous phase are known to a skilled person. For example, the oxygen content can be determined by laser absorption spectroscopy, in particular tuneable diode laser absorption spectroscopy, thus eliminating interference of other components contained in the headspace gas. Specifically, the oxygen content can be determined by means of a device of the type MicroxTX3 from PreSens (Precision Sensing GmbH), whereby the oxygen is measured by fibre optic minisensors via dynamic quenching of luminescence.

It is further preferred that in the gas of the air-tight packaging, the content of inert gas is more than 80 vol-%, preferably more than 84 vol-%, more preferably more than 88 vol-%, more preferably more than 90 vol-%, and most preferably more than 93 vol-% at the time of sealing the packaging. The inert gas may be e.g. nitrogen, argon, other noble gases or mixtures thereof. Given its availability, nitrogen is preferably used. This has the additional advantage that the blister is not deformed due to the oxygen binding by the scavenger. In addition, it increases the life of the scavenger.

According to a preferred embodiment, the gas of the packaging is approximately at atmospheric pressure. However, it may also be advantageous to reduce the pressure in the packaging, i.e. withdraw the gas in the packaging prior to sealing.

According to a preferred embodiment, the oxygen content in the air-tight packaging when sealed under inert gassing with or without an oxygen scavenger is less than 1% oxygen about one week after sealing, preferably less than 0.5%, even more preferably about 0.2% or less. After 12 months without an oxygen scavenger, the oxygen content in the air-tight packaging when sealed under inert gassing is less than 8% oxygen, preferably less than 6% oxygen, more preferably less than 5% oxygen, even more preferably about or less than 4% oxygen. After 12 months with an oxygen scavenger, the oxygen content in the air-tight packaging remains below 1%, preferably below 0.5%, more preferably below 0.2%, most preferably below 0.1% oxygen. Preferably, the same applies after 18 months, more preferably after 24 months, even more preferably after 30 months, most preferably even after 36 months or longer.

The secondary packaging may be transparent, or it may be intransparent. The term "intransparent" refers to material that limits the amount of light that it lets through. Preferably, the amount of light is reduced by at least 50%, more preferably by at least 60%, even more preferably by at least 70%, 80%, 85%, 90%, most preferably by at least 95%. In particular, it is preferred if light of wavelength 250 nm to 790 nm is reduced by at least 50%, more preferably by at least 60%, even more preferably by at least 70%, 80%, 85%, 90%, most preferably by at least 95%.

However, it may be preferred to use transparent secondary packaging, as it allows a visual inspection of the product by the user without breaking the secondary packaging.

An outer packaging, e.g. tertiary packaging, may also be used. Preferably the outer packaging is non-transparent. Preferably, suitable packaging is used so that the product is protected from light.

Therapeutic Treatment

The pharmaceutical product of the invention is preferably for use in the treatment of immunodeficiency disorders, such as Primary or Secondary immunodeficiencies.

Most preferably, the disorder to be treated with the pharmaceutical product of the present invention is selected from the group consisting of congenital agammaglobulinaemia and hypogammaglobulinaemia, common variable immunodeficiency, severe combined immunodeficiency, and IgG subclass deficiencies with recurrent infections.

The treatment may further be a replacement therapy in myeloma or chronic lymphocytic leukaemia with severe secondary hypogammaglobulinaemia and recurrent infections.

The product of the invention may also be used in the treatment of autoimmune diseases and certain neurological diseases, such as Rheumatoid arthritis, Systemic Lupus Erythematosus (SLE), Antiphospholipid syndrome, immune thrombocytopenia (ITP), Kawasaki disease, Guillain Barré syndrome (GBS), multiple sclerosis (MS), chronic inflammatory demyelinating polyneuropathy (CIDP), multifocal motor neuropathy (MMN), myasthenia gravis (MG), skin blistering diseases, scleroderma, Dermatomyositis, Polymyositis, Alzheimer's Disease, Parkinson's Disease, Alzheimer's Disease related to Downs Syndrome, cerebral amyloid angiopathy, Dementia with Lewy bodies, Frontotemporal lobar degeneration or vascular dementia.

The pharmaceutical product can be administered intravenously or subcutaneously, preferably it is administered subcutaneously. In one embodiment, the immunoglobulin solution is administered by the so-called "rapid push" technique described in the review article of R. S. Shapiro (2013, Annals of Allergy, Asthma & Immunology 111 (1) 51-56). According to said technique, a syringe and a butterfly needle is used to push SCIg under the skin as fast as the patient is comfortable with (usually 1 to 2 cc/min). Administration by said technique thus usually takes only between 5 and 20 minutes.

The dose to be administered to the patient ranges from 0.2 to 2 g/kg bodyweight, depending on the condition to be treated. The dose is typically adjusted to the patient's individual needs.

The dose may need to be individualised for each patient dependent on the pharmacokinetic and clinical response and serum IgG trough levels. The following guidelines apply for immunodeficiency conditions: The dose regimen using the subcutaneous route should achieve a sustained level of IgG. A loading dose of at least 0.2 to 0.5 g/kg (1.0 to 2.5 ml/kg) body weight may be required. This may need to be divided over several days. After steady state IgG levels have been attained, maintenance doses are administered at repeated intervals to reach a cumulative monthly dose of the order of 0.4 to 0.8 g/kg (2.0 to 4.0 ml/kg) body weight.

Trough levels should be measured and assessed in conjunction with the patient's clinical response. Depending on the clinical response (e.g. infection rate), adjustment of the dose and/or the dose interval may be considered in order to aim for higher trough levels.

For the treatment of autoimmune or neurological conditions, the doses are usually higher. A trained physician will usually adjust the dose according to the patient's response to the treatment.

EXAMPLES

IgPro20 (trade name Hizentra) is a 20% polyclonal IgG solution, formulated in proline (250 mM) and polysorbate-80, at a pH of 4.8. It is usually provided in glass vials. In order to mitigate discoloration during storage the vials are typically gassed with nitrogen during the filling and stoppering procedures. In addition the vials are stored protected from light. Discoloration of the protein solution is the most sensitive and shelf-life limiting factor for IgPro20.

It was assessed whether IgPro20 may also be stable in COC/COP ready-to-use syringes.

COC/COP syringes have a certain permeability for gases and water vapor. For these reasons different stoppering and (secondary) packaging alternatives were tested: "traditional" stoppering with positioning tube (Setzrohr) and vacuum stoppering.

Example 1: Long Term Stability of IgPro20 in Polymer Syringes: Comparison of Different Syringes and Different Stoppering Techniques Syringes (10 ml) were obtained from four different manufacturers: Schott, Becton Dickinson, Terumo and Daikyo. The syringes were filled with IgPro20 using a peristaltic pump in a laminar flow bench. Alternatively, stoppering was performed with a semi-automatic SVP100 stoppering apparatus from Bausch+Stroebel.

After filling and stoppering, the syringes were stored protected from light without secondary packaging, or were packaged in a gas-tight aluminium multilayer foil from Swisspack. The syringes blistered in the gas-tight aluminium multilayer foil were further divided in two groups: co-packed with and without an oxygen scavenger on iron oxide basis, as alternative one group of syringes were stored with oxygen scavenger on polymer basis.

Subsequently the syringes were stored at 20° C. and 37° C. to assess the stability of the solution under normal and accelerated temperature. Samples were taken and analyzed after 1, 2, 3, 6, 9, 12, 18, 24, 30 and 36 months.

All parameters were measured with standard validated methods, well known to the skilled person.

Analyzed Parameters are:

Discoloration:

UV/VIS Extinction Measurement at 350/500 nm: a photometric method to measure the extinction of the product to detect discoloration. The color intensity is determined by the difference in extinction between a wavelength specific to the color (350 nm) and a reference wavelength (500 nm). The absorbance at the reference wavelength is subtracted to compensate turbidity, non-yellow absorption and opalescence. The final result permits a conclusion about the intensity of the color.

Molecular Size Distribution:

Size-exclusion HPLC, performed according to European Pharmacopoeia 2.2.46 "Chromatographic separation techniques", European Pharmacopoeia 2.2.30 "Size exclusion chromatography", European Pharmacopoeia 0918 "Human Normal Immunoglobulin", and European Pharmacopoeia 0255 "Human Albumin Solution".

Density:

digital densitometer according to European Pharmacopoeia 2.2.5 "Relative Density" and United States Pharmacopoeia method <841>"Specific Gravity".

pH:

pH of a 1% protein solution, according to European Pharmacopoeia 2.2.3 "Potentiometric Determination of pH", European Pharmacopoeia 0918 "Human Immunoglobulin" and European Pharmacopoeia 0255 "Human Albumin Solution".

Fc Function:

Human blood red cell test (complement mediated hemolysis) according to European Pharmacopoeia 2.7.9 "Test for Fc-function in Immunoglobulin": Briefly, human red blood cells of blood group 0 are coated with rubella antigen. The immunoglobulin sample to be tested is added and the mixture is incubated. After addition of guinea pig complement, the lysis of the red blood cells is induced through complement activation by antigen-antibody complexes on the cell surface. The kinetic of haemolysis is measured photometrically as a time dependent absorption at 541 nm and compared against a reference immunoglobulin preparation that has been assessed against the BRP human normal immunoglobulin standard.

Prekallikrein Activator (PKA):

The test is based on the determination of the kallikrein activity according to European Pharmacopoeia 2.6.15 "Prekallikrein Activator". Prekallikrein activator (PKA) activates prekallikrein (PK) to kallikrein, which then converts H-D-prolyl-L-phenylalanyl-L-arginine-p-nitroanilidide dihydrochloride into p-nitroanilinine (pNA) through hydrolysis. The increase in p-nitroaniline is measured photometrically at 405 nm.

Anticomplementary Activity (ACA):

Anticomplementary activity is determined in a hemolysis system using sensitized sheep erythrocytes and human serum as complement source (ACA HS). A specific volume of immunoglobulin solution at 10 mg/ml is incubated with a specific volume of complement. The free complement is then titrated in a hemolysis system using sensitized sheep erythrocytes. The anticomplementary activity is calculated as the ratio of complement consumption to complement control consumption.

Anti-Streptolysin-0 Antibody Content:

The anti-Streptolysin-0 antibody (ASL-0) content is determined by nephelometry. Briefly, polystyrene particles coated with Streptolysin-0 are agglutinated when mixed with samples containing anti-Streptolysin-0 antibodies. The beam of an infrared high performance light diode passed through a cuvette is scattered on the agglutinates. The scattered light is measured with a lens system by a photo detector.

Hepatitis B Antibody Titer (HBs):

The test for the quantitative determination of anti-HBs is a commercially available one-step solid phase enzyme immunoassay (EIA), based on the sandwich principle.

Other non-stability-sensitive parameters, such as aluminium content, polysorbat-80 and proline concentration, protein purity, were also determined.

Results:

For the factors Molecular size distribution, Density, pH, Fc Function, PKA, Anti-Streptolysin-0 and HBs no relevant differences between IgPro20 filled into vials or into polymer syringes (independently from their stoppering technique and secondary packaging) were detected.

Figure 4:
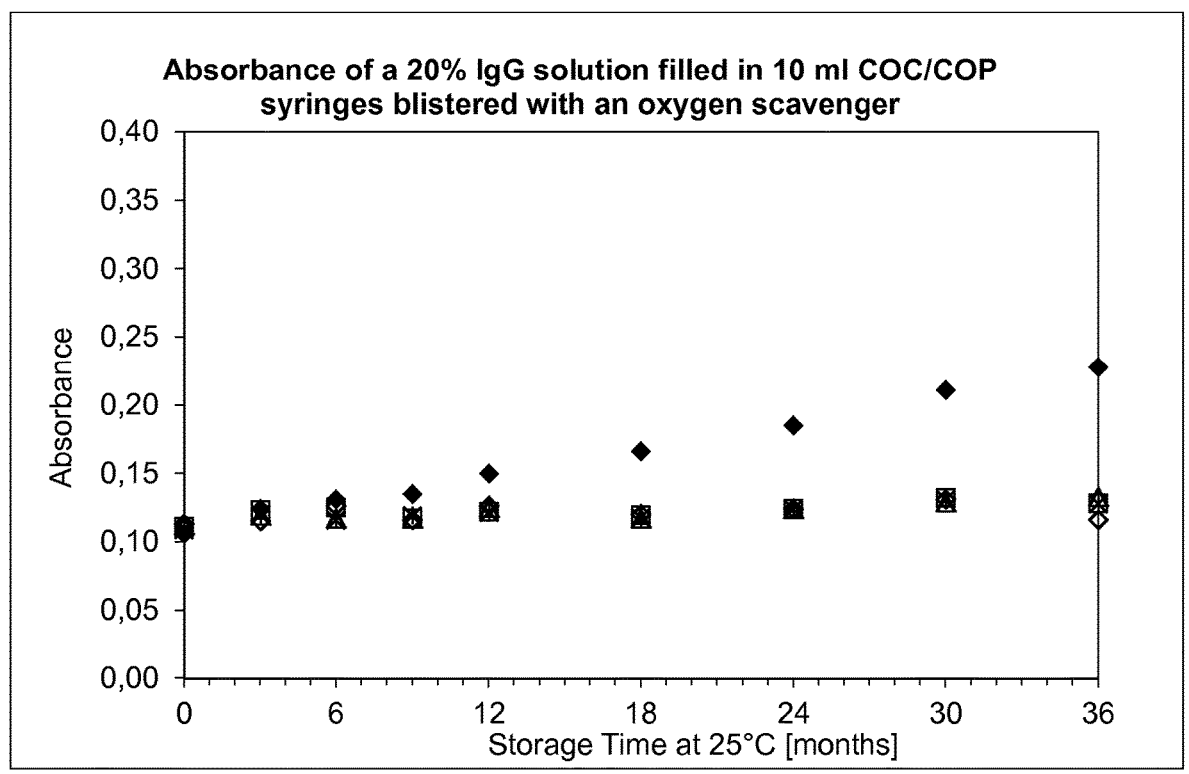
FIG. 4: Absorbance of a 20% IgG solution filled in 10 ml COC/COP syringes blistered with an oxygen scavenger. □ BD Sterifill SCF syringes * Terumo Plajex syringes Δ Daikyo Rezin CZ ◇ Schott TopPac ♦ Reference filling in glass vials

The results are shown in FIGS. 1 to 4. No significant differences were observed between the different syringes tested in this experiment. With increasing storage time, it can be seen that the IgPro20 solution stored in reference glass vials (i.e. glass vials filled and stoppered with inert gassing) show slightly less discoloration, than the IgPro20 stored in syringes without secondary packaging, as measured by absorbance at 350 nm/500 nm (see FIG. 3). However, surprisingly, when the syringes were packaged in sealed secondary packaging with an oxygen scavenger, the IgPro20 showed significantly lower discoloration than in the reference glass vial (FIG. 4).

Similar results were obtained for ACA. When stored in the dark without secondary packaging, over time the IgPro20 filled in syringes showed slightly higher ACA than the IgPro20 in reference glass vials (see FIG. 1). However, surprisingly, when stored in sealed secondary packaging with an oxygen scavenger, the IgPro20 solution in syringes showed significantly lower ACA after longer storage than IgPro20 stored in reference glass vials (see FIG. 2).

Stoppering Technique:

For syringes stored without secondary packaging the stoppering technique was found not to be important. No significant differences in absorbance at 350 nm/500 nm were observed between the samples, regardless of the stoppering technique used.

For syringes sealed in secondary packaging and stored with an oxygen scavenger the stoppering technique was also found not to be relevant. No significant differences in the absorbance at 350 nm/500 nm were found, regardless of the stoppering technique used.

The discoloration of IgPro20 filled into COC/COP syringes blistered without an oxygen scavenger may be slightly less pronounced by syringes stoppered using the vacuum technique, but the difference was judged not to be relevant for the product shelf-life.

The stoppering technique had no influence on ACA.

Example 2: Inert Gassing During Packaging

We found previously that inert gassing of glass vials during filling and stoppering had a beneficial effect on the stability of IgPro20 in glass vials (see WO 2011/104315). Since we found that secondary packaging with an oxygen scavenger was advantageous for the storage of IgPro20 in polymer syringes, we wanted to investigate whether we could further improve storage stability by applying inert gassing during the packaging step.

A series of 5 ml syringes (obtained from Schott) was aseptically filled on a full-scale filling line from Optima. Stoppering occurred traditionally with positioning tube ("Setzrohr"). After visual inspection the syringes were packaged in a highly oxygen tight plastic blister (Sudpack Verpackungen) with or without inert gassing (nitrogen), with or without an oxygen scavenger. The oxygen scavengers were obtained from Standa (ATCO) and Mitsubishi Gas Chemical (Ageless).

The same parameters were tested as in Example 1.

Results:

The positive influence of the oxygen scavenger on discoloration and ACA, and thus on the product shelf life, was confirmed. Inert gassing during blistering showed no additional beneficial effect if an oxygen scavenger was included in the packaging. However, inert gassing could still be useful to limit the amount of oxygen scavenger that is required for long term stability of the IgPro20 in polymer syringes.

The invention claimed is:

1. A pharmaceutical product comprising an air-tight packaging comprising: (a) a pre-filled polymer syringe barrel comprising a polyclonal immunoglobulin solution comprising about 15% (w/v) to about 30% (w/v) IgG and one or more stabilizers, and (b) an oxygen scavenger, wherein the polyclonal immunoglobulin solution does not comprise the oxygen scavenger, wherein the polyclonal immunoglobulin solution is stable over a period of at least 24 months at 25° C. in the polymer syringe barrel, and wherein the polyclonal immunoglobulin solution has a lower absorbance at 350 nm and a lower anticomplementary activity (ACA) after 24 months at 25° C. in the polymer syringe barrel than that of an identical polyclonal immunoglobulin solution stored under identical conditions in a glass vial under inert gas.

2. The pharmaceutical product of claim 1, wherein the polyclonal immunoglobulin solution is to be administered intravenously or subcutaneously.

3. The pharmaceutical product of claim 1, wherein the polyclonal immunoglobulin solution comprises IgG that is at least 95% pure.

4. The pharmaceutical product of claim 1, wherein the one or more stabilizers are amino acid arginine, glycine, proline, or a combination thereof.

5. The pharmaceutical product of claim 1, wherein the polymer syringe barrel is made of or comprises a cycloolefin copolymer, a cycloolefin polymer, or a combination thereof.

6. The pharmaceutical product of claim 1, wherein the polymer syringe barrel is made of or comprises a polypropylene, a polyethylene, a polyacryl, or a polystyrene, or combinations thereof.

7. The pharmaceutical product of claim 1, wherein the interior wall of the polymer syringe barrel is coated prior to filling it.

8. The pharmaceutical product of claim 1, wherein the headspace within the pre-filled polymer syringe barrel is less than 20% of the volume of the polyclonal immunoglobulin solution.

9. The pharmaceutical product of claim 1, wherein the air-tight packaging is not transparent.

10. The pharmaceutical product of claim 1, wherein the air-tight packaging is transparent.

11. The pharmaceutical product of claim 1, wherein the air-tight packaging is a blister pack or a sealed pouch.

12. The pharmaceutical product of claim 1, wherein the oxygen scavenger is iron oxide.

13. The pharmaceutical product of claim 1, wherein the air-tight packaging has been filled with inert gas.

14. The pharmaceutical product of claim 1, wherein the polyclonal immunoglobulin solution is protected from light.

15. The pharmaceutical product of claim 1, wherein the polymer syringe barrel is suitable for insertion or attachment to a catheter, a syringe driver, a pumping device, or an autoinjector.

16. The pharmaceutical product of claim 1, wherein the polymer syringe barrel is suitable for transferring the product directly or via tip-to-tip connector to the reservoir of an infusion pump or an autoinjector, or to another syringe suitable for a syringe pump or syringe driver.

17. The pharmaceutical product of claim 1, wherein a needle is attached to the polymer syringe barrel, having a gauge value from 20 to 30G.

18. The pharmaceutical product of claim 14, wherein the polyclonal immunoglobulin solution is protected from light by the packaging.

19. The pharmaceutical product of claim 1, wherein the polyclonal immunoglobulin solution is stable over a period of at least 30 months in the polymer syringe barrel.

20. The pharmaceutical product of claim 1, wherein the polyclonal immunoglobulin solution is stable over a period of at least 36 months in the polymer syringe barrel.

21. The pharmaceutical product of claim 1, wherein the polyclonal immunoglobulin solution comprises about 18% (w/v) to about 25% (w/v) IgG.

22. The pharmaceutical product of claim 1, wherein the polyclonal immunoglobulin solution comprises about 20% (w/v) IgG.

23. The pharmaceutical product of claim 1, wherein the pre-filled syringe barrel is within an air-tight secondary packaging.

24. The pharmaceutical product of claim 23, wherein the oxygen scavenger is contained in the interior of the secondary packaging and outside of the syringe barrel.

25. The pharmaceutical product of claim 23, wherein the oxygen scavenger is incorporated in the material of the secondary packaging.

26. The pharmaceutical product of claim 1, wherein the oxygen scavenger is incorporated in the material of the pre-filled syringe barrel.

27. The pharmaceutical product of claim 1, wherein the packaging does not comprise a syringe plunger rod.

28. A pharmaceutical product comprising an air-tight packaging comprising: (a) a pre-filled polymer syringe barrel comprising a polyclonal immunoglobulin solution comprising about 15% (w/v) to about 30% (w/v) IgG and one or more stabilizers, and (b) an oxygen scavenger, wherein the polyclonal immunoglobulin solution does not comprise the oxygen scavenger, wherein the polyclonal immunoglobulin solution is stable over a period of at least 24 months at 25° C. in the polymer syringe barrel, wherein the one or more stabilizers are amino acid arginine, glycine, proline, or a combination thereof, and wherein the headspace within the pre-filled polymer syringe barrel is less than 20% of the volume of the polyclonal immunoglobulin solution, and wherein the polyclonal immunoglobulin solution has a lower absorbance at 350 nm and a lower anticomplementary activity (ACA) after 24 months at 25° C. in the polymer syringe barrel than that of an identical polyclonal immunoglobulin solution stored under identical conditions in a glass vial under inert gas.

29. The pharmaceutical product of claim 28, wherein the polyclonal immunoglobulin solution is stable over a period of at least 36 months at 25° C. in the polymer syringe barrel.

30. The pharmaceutical product of claim 1, wherein the inner wall of the syringe barrel is siliconized.

31. The pharmaceutical product of claim 28, wherein the inner wall of the syringe barrel is siliconized.

* * * * *